(12) United States Patent
Unanue et al.

(10) Patent No.: US 12,153,056 B2
(45) Date of Patent: Nov. 26, 2024

(54) COMPOSITIONS FOR AND METHODS OF DIAGNOSING, PROGNOSING, AND TREATING DIABETES

(71) Applicants: Emil R. Unanue, St. Louis, MO (US); Xiaoxiao Wan, St. Louis, MO (US); Cheryl Lichti, St. Louis, MO (US)

(72) Inventors: Emil R. Unanue, St. Louis, MO (US); Xiaoxiao Wan, St. Louis, MO (US); Cheryl Lichti, St. Louis, MO (US)

(73) Assignee: Washington University, St. Louis, MO (US)

( * ) Notice: Subject to any disclaimer, the term of this patent is extended or adjusted under 35 U.S.C. 154(b) by 454 days.

(21) Appl. No.: 16/929,411

(22) Filed: Jul. 15, 2020

(65) Prior Publication Data

US 2021/0018520 A1  Jan. 21, 2021

Related U.S. Application Data

(60) Provisional application No. 62/874,227, filed on Jul. 15, 2019.

(51) Int. Cl.
| | |
|---|---|
| *G01N 33/74* | (2006.01) |
| *C07K 16/26* | (2006.01) |
| *G01N 33/50* | (2006.01) |
| *G01N 33/68* | (2006.01) |

(52) U.S. Cl.
CPC .............. *G01N 33/74* (2013.01); *C07K 16/26* (2013.01); *C07K 2317/76* (2013.01); *G01N 33/505* (2013.01); *G01N 33/6848* (2013.01); *G01N 2333/62* (2013.01); *G01N 2800/042* (2013.01); *G01N 2800/50* (2013.01); *G01N 2800/52* (2013.01)

(58) Field of Classification Search
CPC ......... G01N 2333/62; G01N 2800/042; G01N 33/505
See application file for complete search history.

(56) References Cited

U.S. PATENT DOCUMENTS

| | | | |
|---|---|---|---|
| 2004/0126374 A1 | 7/2004 | Zaghouani et al. | |
| 2018/0118801 A1 | 5/2018 | Delong et al. | |

FOREIGN PATENT DOCUMENTS

| | | |
|---|---|---|
| WO | WO 01/30378 | 5/2001 |
| WO | WO 2006/096565 | 9/2006 |
| WO | WO 2010/141658 | 12/2010 |
| WO | WO 2012/007950 | 1/2012 |
| WO | WO 2012/162697 | 11/2012 |

OTHER PUBLICATIONS

Delong et al., Pathogenic CD4 T cells in type 1 diabetes recognize epitopes formed by peptide fusion, 2016, Science, vol. 351, Issue 6274, pp. 1-12 (Year: 2016).*
Taylor et al., A high-throughput mass spectrometry assay to simultaneously measure intact insulin and C-peptide, 2016, Clinica Chimica Acta, vol. 455, pp. 202-208 (Year: 2016).*
Kinumi et al., Quantification of serum C-peptide by isotope-dilution liquid chromatography-tandem mass spectrometry: Enhance detection using chemical modification and immunoaffinity purification, 2014, Journal of Chromatography B, pp. 138-142 (Year: 2014).*
Wan et al., Pancreatic islets communicate with lymphoid tissues via exocytosis of insulin peptides, 2018, Nature, vol. 560, Issue 7716, pp. 1-27 (Year: 2018).*
Leighton et al., A Practical Review of C-Peptide Testing in Diabetes, 2017, Diabetes Therapy, vol. 8, pp. 475-487 (Year: 2017).*
Unanue, Antigen Presentation in the Autoimmune Diabetes of the NOD Mouse, 2014, Annual Review of Immunology, vol. 32, pp. 579-608 (Year: 2014).*
Boone and Adamec, Top-Down Proteomics, 2016, Proteomic Profiling and Analytical Chemistry, Second Edition (Year: 2016).*
Crawford et al., Specificity and detection of insulin-reactive CD4+ T cells in type 1 diabetes in the nonobese diabetic (NOD) mouse, 2011, PNAS, vol. 108, No. 40, pp. 16729-16734 (Year: 2011).*
Roep and Peakman, Antigen Targets of Type 1 Diabetes Autoimmunity, 2012, Cold Harbor Perspectives in Medicine, vol. 201, Issue 2, pp. 1-14 (Year: 2012).*
VIVO Pathophysiology, Insulin Synthesis and Secretion, 2018, retrieved from: http://www.vivo.colostate.edu/hbooks/pathphys/endocrine/pancreas/insulin.html#:~: text=Biosynthesis%20of%20Insulin&text=Within%20the%20endoplasmic%20reticulum%2C%20proinsulin, which%20accumulate%20in%20the%20cyto (Year: 2018).*
Chen et al., An efficient two-step subcellular fractionation method for the enrichment of insulin granules from INS-1 cells, 2015, Biophysics Reports, vol. 1, Issue 1, pp. 34-40 (Year: 2015).*
Aly, H. et al. A novel strategy to increase the proliferative potential of adult human β-cells while maintaining their differentiated phenotype. *PLoS One* 8, e66131 (2013).
Buck, M. D., O'Sullivan, D. & Pearce, E. L. T cell metabolism drives immunity. *J. Exp. Med.* 212, 1345-1360 (2015).
Caparrós, Shifting Central Tolerance In Type 1 Diabetes, Tolerance Induction By Presenting Peptides In Non-Obese Diabetic Mice, Autonomous University of Barcelona, created on May 15, 2015, 1 page.
Chen, W. et al. Evidence that a peptide spanning the B-C junction of proinsulin is an early Autoantigen epitope in the pathogenesis of type 1 diabetes. *J. Immunol.* 167, 4926-4935 (2001).
Constantinides, M. G., Picard, D., Savage, A. K. & Bendelac, A. A naive-like population of human CD1d-restricted T cells expressing intermediate levels of promyelocytic leukemia zinc finger. *J. Immunol.* 187, 309-315 (2011).
Egen, J. G. et al. Intravital imaging reveals limited antigen presentation and T cell effector function in mycobacterial granulomas. *Immunity* 34, 807-819 (2011).

(Continued)

*Primary Examiner* — Jeffrey Stucker
*Assistant Examiner* — Brittney E Donoghue

(57) ABSTRACT

Among the various aspects of the present disclosure is the provision of compositions for and methods of diagnosing, prognosing, and treating diabetes.

18 Claims, 14 Drawing Sheets
(12 of 14 Drawing Sheet(s) Filed in Color)
Specification includes a Sequence Listing.

(56) References Cited

OTHER PUBLICATIONS

Eickhoff, S. et al. Robust anti-viral immunity requires multiple distinct T cell-dendritic cell interactions. *Cell* 162, 1322-1337 (2015).

Ferris, S. T. et al. The islet-resident macrophage is in an inflammatory state and senses microbial products in blood. *J. Exp. Med.* 214, 2369-2385 (2017).

Gardner, J. M. et al. Deletional tolerance mediated by extrathymic Aire-expressing cells. *Science* 321, 843-847 (2008).

Halban, P. A. & Wollheim, C. B. Intracellular degradation of insulin stores by rat pancreatic islets in vitro. An alternative pathway for homeostasis of pancreatic insulin content. *J. Biol. Chem.* 255, 6003-6006 (1980).

Kaech, S. M., Hemby, S., Kersh, E. & Ahmed, R. Molecular and functional profiling of memory CD8 T cell differentiation. *Cell* 111, 837-851 (2002).

Kalekar, L. A. et al. CD4+ T cell anergy prevents autoimmunity and generates regulatory T cell precursors. *Nat. Immunol.* 17, 304-314 (2016).

Lamont, D. et al. Compensatory mechanisms allow undersized anchor-deficient class I MHC ligands to mediate pathogenic autoreactive T cell responses. *J. Immunol.* 193, 2135-2146 (2014).

Le Borgne, M. et al. The impact of negative selection on thymocyte migration in the medulla. *Nat. Immunol.* 10, 823-830 (2009).

Levisetti et al., The Insulin-Specific T Cells of Nonobese Diabetic Mice Recognize a Weak MHC-Binding Segment in More Than One Form, J Immunol May 15, 2007, 178 (10) 6051-6057; DOI: https://doi.org/10.4049/jimmunol.178.10.6051.

Levisetti, M. G., Suri, A., Frederick, K. & Unanue, E. R. Absence of lymph nodes in NOD mice treated with lymphotoxin-β receptor immunoglobulin protects from diabetes. *Diabetes* 53, 3115-3119 (2004).

Macián, F. et al. Transcriptional mechanisms underlying lymphocyte tolerance. *Cell* 109, 719-731 (2002).

Mohan et al., Register shifting of an insulin peptide-MHC complex allows diabetogenic T cells to escape thymic deletion, J Exp Med. Nov. 21, 2011; 208(12): 2375-2383. doi: 10.1084/jem.20111502.

Mohan, J. F. et al. Unique autoreactive T cells recognize insulin peptides generated within the islets of Langerhans in autoimmune diabetes. *Nat. Immunol.* 11, 350-354 (2010).

Mohan, J. F., Calderon, B., Anderson, M. S. & Unanue, E. R. Pathogenic CD4+ T cells recognizing an unstable peptide of insulin are directly recruited into islets bypassing local lymph nodes. J. Exp. Med. 210, 2403-2414 (2013).

Nakayama, M. et al. Prime role for an insulin epitope in the development of type 1 diabetes in NOD mice. *Nature* 435, 220-223 (2005).

Pugliese, Autoreactive T cells in type 1 diabetes, The Journal of Clinical Investigation, Review, vol. 127, No. 8 (Aug. 2017).

Schäffer, L. et al. A novel high-affinity peptide antagonist to the insulin receptor. *Biochem. Biophys. Res. Commun.* 376, 380-383 (2008).

Schietinger, A., Delrow, J. J., Basom, R. S., Blattman, J. N. & Greenberg, P. D. Rescued tolerant CD8 T cells are preprogrammed to reestablish the tolerant state. *Science* 335, 723-727 (2012).

Smith, R. E. & Farquhar, M. G. Lysosome function in the regulation of the secretory process in cells of the anterior pituitary gland. *J. Cell Biol.* 31, 319-347 (1966).

Unanue, E. R. Antigen presentation in the autoimmune diabetes of the NOD mouse. *Annu. Rev. Immunol.* 32, 579-608 (2014).

Verdaguer, J. et al. Spontaneous autoimmune diabetes in monoclonal T cell nonobese diabetic mice. *J. Exp. Med.* 186, 1663-1676 (1997).

Vomund, A. N. et al. Beta cells transfer vesicles containing insulin to phagocytes for presentation to T cells. *Proc. Natl Acad. Sci. USA* 112, E5496-E5502 (2015).

Wan, X. & Unanue, E. R. Unique features in the presentation of insulin epitopes in autoimmune diabetes: an update. *Curr. Opin. Immunol.* 46, 30-37 (2017).

Wan, X., Thomas, J. W. & Unanue, E. R. Class-switched anti-insulin antibodies originate from unconventional antigen presentation in multiple lymphoid sites. *J. Exp. Med.* 213, 967-978 (2016).

Weckman, A. et al. Autophagy in the endocrine glands. *J. Mol. Endocrinol.* 52, R151-R163 (2014).

Wherry, E. J. et al. Molecular signature of CD8+ T cell exhaustion during chronic viral infection. *Immunity* 27, 670-684 (2007).

Wong, F. S. et al. Identification of an MHC class I-restricted autoantigen in type 1 diabetes by screening an organ-specific cDNA library. *Nat. Med.* 5, 1026-1031 (1999).

Yang, J. et al. Autoreactive T cells specific for insulin B:11-23 recognize a low-affinity peptide register in human subjects with autoimmune diabetes. *Proc. Natl Acad. Sci. USA* 111, 14840-14845 (2014).

Zhang et al. Monoclonal antibody blocking the recognition of an insulin peptide-MHC complex modulates type 1 diabetes Proc Natl Acad Sci U S A. Feb. 18, 2014; 111(7): 2656-2661. Published online Feb. 3, 2014. doi: 10.1073/pnas.1323436111.

Zinselmeyer, B. H. et al. In situ characterization of CD4+ T cell behavior in mucosal and systemic lymphoid tissues during the induction of oral priming and tolerance. *J. Exp. Med.* 201, 1815-1823 (2005).

\* cited by examiner

SEQUENCE LISTING

```
<160> NUMBER OF SEQ ID NOS: 51

<210> SEQ ID NO 1
<211> LENGTH: 10
<212> TYPE: PRT
<213> ORGANISM: Homo sapiens

<400> SEQUENCE: 1

Phe Val Asn Gln His Leu Cys Gly Ser His
1               5                   10

<210> SEQ ID NO 2
<211> LENGTH: 13
<212> TYPE: PRT
<213> ORGANISM: Homo sapiens

<400> SEQUENCE: 2

Phe Val Asn Gln His Leu Cys Gly Ser His Leu Val Glu
1               5                   10

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 30
<212> TYPE: PRT
<213> ORGANISM: Homo sapiens
<220> FEATURE:
<221> NAME/KEY: MOD_RES
<222> LOCATION: (7)..(19)
<223> OTHER INFORMATION: Xaa indicates cysteic acid

<400> SEQUENCE: 4

Phe Val Asn Gln His Leu Xaa Gly Ser His Leu Val Glu Ala Leu Tyr
1               5                   10                  15
```

```
Leu Val Xaa Gly Glu Arg Gly Phe Phe Tyr Thr Pro Lys Thr
            20              25                  30
```

<210> SEQ ID NO 5
<211> LENGTH: 7
<212> TYPE: PRT
<213> ORGANISM: Homo sapiens

<400> SEQUENCE: 5

```
His Leu Val Glu Ala Leu Tyr
1               5
```

<210> SEQ ID NO 6
<211> LENGTH: 20
<212> TYPE: PRT
<213> ORGANISM: Homo sapiens

<400> SEQUENCE: 6

```
Leu Val Glu Ala Leu Tyr Leu Val Cys Gly Glu Arg Gly Phe Phe Tyr
1               5                   10                  15

Thr Pro Lys Thr
            20
```

<210> SEQ ID NO 7
<211> LENGTH: 10
<212> TYPE: PRT
<213> ORGANISM: Homo sapiens

<400> SEQUENCE: 7

```
Gly Glu Arg Gly Phe Phe Tyr Thr Pro Lys
1               5                   10
```

<210> SEQ ID NO 8
<211> LENGTH: 11
<212> TYPE: PRT
<213> ORGANISM: Homo sapiens

<400> SEQUENCE: 8

```
Gly Glu Arg Gly Phe Phe Tyr Thr Pro Lys Thr
1               5                   10
```

<210> SEQ ID NO 9
<211> LENGTH: 10
<212> TYPE: PRT
<213> ORGANISM: Homo sapiens

<400> SEQUENCE: 9

```
Glu Arg Gly Phe Phe Tyr Thr Pro Lys Thr
1               5                   10
```

<210> SEQ ID NO 10
<211> LENGTH: 8
<212> TYPE: PRT
<213> ORGANISM: Homo sapiens

<400> SEQUENCE: 10

```
Gly Phe Phe Tyr Thr Pro Lys Thr
1               5
```

<210> SEQ ID NO 11
<211> LENGTH: 6
<212> TYPE: PRT
<213> ORGANISM: Homo sapiens

```
<400> SEQUENCE: 11

Phe Phe Tyr Thr Pro Lys
1               5

<210> SEQ ID NO 12
<211> LENGTH: 7
<212> TYPE: PRT
<213> ORGANISM: Homo sapiens

<400> SEQUENCE: 12

Phe Phe Tyr Thr Pro Lys Thr
1               5

<210> SEQ ID NO 13
<211> LENGTH: 32
<212> TYPE: PRT
<213> ORGANISM: Homo sapiens

<400> SEQUENCE: 13

Arg Glu Ala Glu Asp Leu Gln Val Gly Gln Val Glu Leu Gly Gly Gly
1               5                   10                  15

Pro Gly Ala Gly Ser Leu Gln Pro Leu Ala Leu Glu Gly Ser Leu Gln
            20                  25                  30

<210> SEQ ID NO 14
<211> LENGTH: 8
<212> TYPE: PRT
<213> ORGANISM: Homo sapiens

<400> SEQUENCE: 14

Glu Ala Glu Asp Leu Gln Val Gly
1               5

<210> SEQ ID NO 15
<211> LENGTH: 9
<212> TYPE: PRT
<213> ORGANISM: Homo sapiens

<400> SEQUENCE: 15

Glu Ala Glu Asp Leu Gln Val Gly Gln
1               5

<210> SEQ ID NO 16
<211> LENGTH: 11
<212> TYPE: PRT
<213> ORGANISM: Homo sapiens

<400> SEQUENCE: 16

Glu Ala Glu Asp Leu Gln Val Gly Gln Val Glu
1               5                   10

<210> SEQ ID NO 17
<211> LENGTH: 12
<212> TYPE: PRT
<213> ORGANISM: Homo sapiens

<400> SEQUENCE: 17

Glu Ala Glu Asp Leu Gln Val Gly Gln Val Glu Leu
1               5                   10

<210> SEQ ID NO 18
<211> LENGTH: 13
<212> TYPE: PRT
<213> ORGANISM: Homo sapiens
```

<400> SEQUENCE: 18

Glu Ala Glu Asp Leu Gln Val Gly Gln Val Glu Leu Gly
1               5                   10

<210> SEQ ID NO 19
<211> LENGTH: 14
<212> TYPE: PRT
<213> ORGANISM: Homo sapiens

<400> SEQUENCE: 19

Glu Ala Glu Asp Leu Gln Val Gly Gln Val Glu Leu Gly Gly
1               5                   10

<210> SEQ ID NO 20
<211> LENGTH: 30
<212> TYPE: PRT
<213> ORGANISM: Homo sapiens
<220> FEATURE:
<221> NAME/KEY: MOD_RES
<222> LOCATION: (7)..(19)
<223> OTHER INFORMATION: Xaa indicates cysteic acid

<400> SEQUENCE: 20

Phe Val Asn Gln His Leu Xaa Gly Ser His Leu Val Glu Ala Leu Tyr
1               5                   10                  15
Leu Val Xaa Gly Glu Arg Gly Phe Phe Tyr Thr Pro Lys Thr
            20                  25                  30

<210> SEQ ID NO 21
<211> LENGTH: 7
<212> TYPE: PRT
<213> ORGANISM: Homo sapiens

<400> SEQUENCE: 21

His Leu Val Glu Ala Leu Tyr
1               5

<210> SEQ ID NO 22
<211> LENGTH: 11
<212> TYPE: PRT
<213> ORGANISM: Homo sapiens

<400> SEQUENCE: 22

Gly Glu Arg Gly Phe Phe Tyr Thr Pro Lys Thr
1               5                   10

<210> SEQ ID NO 23
<211> LENGTH: 10
<212> TYPE: PRT
<213> ORGANISM: Homo sapiens

<400> SEQUENCE: 23

Glu Arg Gly Phe Phe Tyr Thr Pro Lys Thr
1               5                   10

<210> SEQ ID NO 24
<211> LENGTH: 8
<212> TYPE: PRT
<213> ORGANISM: Homo sapiens

<400> SEQUENCE: 24

Gly Phe Phe Tyr Thr Pro Lys Thr
1               5

```
<210> SEQ ID NO 25
<211> LENGTH: 7
<212> TYPE: PRT
<213> ORGANISM: Homo sapiens

<400> SEQUENCE: 25

Phe Phe Tyr Thr Pro Lys Thr
1               5

<210> SEQ ID NO 26
<211> LENGTH: 32
<212> TYPE: PRT
<213> ORGANISM: Homo sapiens

<400> SEQUENCE: 26

Arg Glu Ala Glu Asp Leu Gln Val Gly Gln Val Glu Leu Gly Gly
1               5                   10                  15

Pro Gly Ala Gly Ser Leu Gln Pro Leu Ala Leu Glu Gly Ser Leu Gln
            20                  25                  30

<210> SEQ ID NO 27
<211> LENGTH: 9
<212> TYPE: PRT
<213> ORGANISM: Homo sapiens

<400> SEQUENCE: 27

Glu Ala Glu Asp Leu Gln Val Gly Gln
1               5

<210> SEQ ID NO 28
<211> LENGTH: 11
<212> TYPE: PRT
<213> ORGANISM: Homo sapiens

<400> SEQUENCE: 28

Glu Ala Glu Asp Leu Gln Val Gly Gln Val Glu
1               5                   10

<210> SEQ ID NO 29
<211> LENGTH: 12
<212> TYPE: PRT
<213> ORGANISM: Homo sapiens

<400> SEQUENCE: 29

Glu Ala Glu Asp Leu Gln Val Gly Gln Val Glu Leu
1               5                   10

<210> SEQ ID NO 30
<211> LENGTH: 8
<212> TYPE: PRT
<213> ORGANISM: Homo sapiens

<400> SEQUENCE: 30

Tyr Gln Leu Glu Asn Tyr Cys Asn
1               5

<210> SEQ ID NO 31
<211> LENGTH: 15
<212> TYPE: PRT
<213> ORGANISM: Mus musculus

<400> SEQUENCE: 31

Glu Val Glu Asp Thr Pro Val Arg Ser Gly Ser Asn Pro Gln Met
1               5                   10                  15
```

```
<210> SEQ ID NO 32
<211> LENGTH: 13
<212> TYPE: PRT
<213> ORGANISM: Mus musculus

<400> SEQUENCE: 32

Glu Val Glu Asp Pro Gln Val Ala Glu Val Ala Arg Gln
1               5                   10

<210> SEQ ID NO 33
<211> LENGTH: 43
<212> TYPE: PRT
<213> ORGANISM: Mus musculus

<400> SEQUENCE: 33

Gly Ser Leu Asp Glu Ser Phe Tyr Asp Trp Phe Glu Arg Gln Leu Gly
1               5                   10                  15

Gly Gly Ser Gly Gly Ser Ser Leu Glu Glu Glu Trp Ala Gln Ile Gln
            20                  25                  30

Cys Glu Val Trp Gly Arg Gly Cys Pro Ser Tyr
        35                  40

<210> SEQ ID NO 34
<211> LENGTH: 30
<212> TYPE: PRT
<213> ORGANISM: Homo sapiens

<400> SEQUENCE: 34

Phe Val Lys Gln His Leu Cys Gly Pro His Leu Val Glu Ala Leu Tyr
1               5                   10                  15

Leu Val Cys Gly Glu Arg Gly Phe Phe Tyr Thr Pro Lys Ser
            20                  25                  30

<210> SEQ ID NO 35
<211> LENGTH: 30
<212> TYPE: PRT
<213> ORGANISM: Homo sapiens

<400> SEQUENCE: 35

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Met Ser
            20                  25                  30

<210> SEQ ID NO 36
<211> LENGTH: 15
<212> TYPE: PRT
<213> ORGANISM: Homo sapiens

<400> SEQUENCE: 36

Ser His Leu Val Glu Ala Leu Tyr Leu Val Cys Gly Glu Arg Gly
1               5                   10                  15

<210> SEQ ID NO 37
<211> LENGTH: 13
<212> TYPE: PRT
<213> ORGANISM: Homo sapiens

<400> SEQUENCE: 37

Leu Val Glu Ala Leu Tyr Leu Val Cys Gly Glu Arg Gly
1               5                   10
```

```
<210> SEQ ID NO 38
<211> LENGTH: 20
<212> TYPE: PRT
<213> ORGANISM: Homo sapiens

<400> SEQUENCE: 38

Leu Val Glu Ala Leu Tyr Leu Val Cys Gly Glu Arg Gly Phe Phe Tyr
1               5                   10                  15

Thr Pro Lys Ser
            20

<210> SEQ ID NO 39
<211> LENGTH: 11
<212> TYPE: PRT
<213> ORGANISM: Homo sapiens

<400> SEQUENCE: 39

Val Glu Ala Leu Tyr Leu Val Cys Gly Glu Arg
1               5                   10

<210> SEQ ID NO 40
<211> LENGTH: 12
<212> TYPE: PRT
<213> ORGANISM: Homo sapiens

<400> SEQUENCE: 40

Val Glu Ala Leu Tyr Leu Val Cys Gly Glu Arg Gly
1               5                   10

<210> SEQ ID NO 41
<211> LENGTH: 18
<212> TYPE: PRT
<213> ORGANISM: Homo sapiens

<400> SEQUENCE: 41

Glu Ala Leu Tyr Leu Val Cys Gly Glu Arg Gly Phe Phe Tyr Thr Pro
1               5                   10                  15

Lys Ser

<210> SEQ ID NO 42
<211> LENGTH: 9
<212> TYPE: PRT
<213> ORGANISM: Homo sapiens

<400> SEQUENCE: 42

Leu Tyr Leu Val Cys Gly Glu Arg Gly
1               5

<210> SEQ ID NO 43
<211> LENGTH: 10
<212> TYPE: PRT
<213> ORGANISM: Homo sapiens

<400> SEQUENCE: 43

Ser Leu Tyr Gln Leu Glu Asn Tyr Cys Asn
1               5                   10

<210> SEQ ID NO 44
<211> LENGTH: 7
<212> TYPE: PRT
<213> ORGANISM: Homo sapiens

<400> SEQUENCE: 44
```

```
Tyr Gln Leu Glu Asn Tyr Cys
1               5
```

<210> SEQ ID NO 45
<211> LENGTH: 31
<212> TYPE: PRT
<213> ORGANISM: Homo sapiens

<400> SEQUENCE: 45

```
Phe Tyr Thr Pro Lys Ser Arg Arg Glu Val Glu Asp Pro Gln Val Glu
1               5                   10                  15

Gln Leu Glu Leu Gly Gly Ser Pro Gly Asp Leu Gln Thr Leu Ala
            20                  25                  30
```

<210> SEQ ID NO 46
<211> LENGTH: 28
<212> TYPE: PRT
<213> ORGANISM: Homo sapiens

<400> SEQUENCE: 46

```
Tyr Thr Pro Lys Ser Arg Arg Glu Val Glu Asp Pro Gln Val Glu Gln
1               5                   10                  15

Leu Glu Leu Gly Gly Ser Pro Gly Asp Leu Gln Thr
            20                  25
```

<210> SEQ ID NO 47
<211> LENGTH: 29
<212> TYPE: PRT
<213> ORGANISM: Homo sapiens

<400> SEQUENCE: 47

```
Tyr Thr Pro Met Ser Arg Arg Glu Val Glu Asp Pro Gln Val Ala Gln
1               5                   10                  15

Leu Glu Leu Gly Gly Gly Pro Gly Ala Gly Asp Leu Gln
            20                  25
```

<210> SEQ ID NO 48
<211> LENGTH: 30
<212> TYPE: PRT
<213> ORGANISM: Homo sapiens

<400> SEQUENCE: 48

```
Tyr Thr Pro Lys Ser Arg Arg Glu Val Glu Asp Pro Gln Val Glu Gln
1               5                   10                  15

Leu Glu Leu Gly Gly Ser Pro Gly Asp Leu Gln Thr Leu Ala
            20                  25                  30
```

<210> SEQ ID NO 49
<211> LENGTH: 30
<212> TYPE: PRT
<213> ORGANISM: Homo sapiens

<400> SEQUENCE: 49

```
Tyr Thr Pro Met Ser Arg Arg Glu Val Glu Asp Pro Gln Val Ala Gln
1               5                   10                  15

Leu Glu Leu Gly Gly Gly Pro Gly Ala Gly Asp Leu Gln Thr
            20                  25                  30
```

<210> SEQ ID NO 50
<211> LENGTH: 32
<212> TYPE: PRT
<213> ORGANISM: Homo sapiens

```
<400> SEQUENCE: 50

Tyr Thr Pro Met Ser Arg Arg Glu Val Glu Asp Pro Gln Val Ala Gln
1               5                   10                  15

Leu Glu Leu Gly Gly Gly Pro Gly Ala Gly Asp Leu Gln Thr Leu Ala
            20                  25                  30

<210> SEQ ID NO 51
<211> LENGTH: 15
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Xaa indicates cysteic acid

<400> SEQUENCE: 51

Ser His Leu Val Glu Ala Leu Tyr Leu Val Xaa Gly Glu Arg Gly
1               5                   10                  15
```

COMPOSITIONS FOR AND METHODS OF DIAGNOSING, PROGNOSING, AND TREATING DIABETES

CROSS-REFERENCE TO RELATED APPLICATIONS

This application claims priority from U.S. Provisional Application Ser. No. 62/874,227 filed on 15 Jul. 2019, which is incorporated herein by reference in its entirety.

STATEMENT REGARDING FEDERALLY SPONSORED RESEARCH OR DEVELOPMENT

This invention was made with government support under grant number DK058177 and AI114551 awarded by National Institutes of Health. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to diabetes treatment and diagnoses.

SUMMARY OF THE INVENTION

Among the various aspects of the present disclosure is the provision of compositions for and methods of diagnosing, prognosing, and treating diabetes.

An aspect of the present disclosure provides for a method of detecting insulin peptides comprising: administering glucose to a subject; obtaining a biological sample comprising insulin peptides (e.g., the biological sample comprising circulating blood cells or circulating leukocytes); and/or detecting a level of an immunogenic insulin peptide, wherein the immunogenic insulin peptide comprises a pathogenic epitope.

In some embodiments, the biological sample comprises circulating blood cells or circulating leukocytes.

In some embodiments, the immunogenic insulin peptide is a peptide fragment catabolized from insulin released from pancreatic islets into blood.

In some embodiments, the immunogenic insulin peptide is recognized by insulin-specific CD4 T cells. In some embodiments, the insulin-specific CD4 T cells are segment 12-20 insulin B-chain (B:12-20)-specific CD4 T cells recognizing a B:12-20 epitope. In some embodiments, the B:12-20-specific T cells have reduced motility when in fluid contact with immunogenic insulin peptides compared to a control in fluid contact with the immunogenic insulin peptides. In some embodiments, the control is a wild-type CD4 T cell.

In some embodiments, the level of an immunogenic insulin peptide is detected using mass spectrometry. In some embodiments, peptide components in the biological sample are separated with a gradient: all % Buffer B (0.1% formic acid in ACN): at about 0-40 min, at about 2-22%; at about 40-50 min, at about 22-35%; at about 50-60 min, at about 35-95%; at about 60-70 min, isocratic at about 95%; at about 70-71 min, at about 95-2%; and at about 71-85 min, at about isocratic at 2%.

In some embodiments, the method further comprises: comparing a level of immunogenic insulin peptides to a level of immunogenic insulin peptides of a control or subject not having T1D; comparing a level of immunogenic insulin peptides to a level of immunogenic insulin peptides of the subject prior to T1 D treatment; or comparing a level of immunogenic insulin peptides to a level of immunogenic insulin peptides of the subject to the level of immunogenic insulin peptides at an earlier time.

In some embodiments, if the level of an immunogenic insulin peptide is elevated compared to a control, the subject is diagnosed with T1D or is determined to be at risk for developing T1D.

In some embodiments, if the level of an immunogenic insulin peptide is elevated compared to the level of an immunogenic insulin peptide prior to treatment, the subject is determined to be not responding to treatment.

In some embodiments, if the level of an immunogenic insulin peptide is equivalent or reduced compared to the level of an immunogenic insulin peptide prior to treatment, the subject is determined to be responding to treatment.

In some embodiments, an increased level of immunogenic insulin peptides compared to the level of an immunogenic insulin peptide of the subject at an earlier time, indicates the subject has an increased stage of disease.

In some embodiments, an increased level of immunogenic insulin peptides compared to a control not having T1D or the subject at an earlier time, the subject is diagnosed with T1D or increased risk of having T1 D.

In some embodiments, the immunogenic insulin peptide comprises an immunogenic insulin peptide epitope, immunogenic portion of an immunogenic insulin peptide, or immunogenic mutant of an insulin peptide and is capable of eliciting an autoimmune response in the subject.

In some embodiments, the immunogenic insulin peptide is a peptide derived from an insulin B chain.

In some embodiments, the immunogenic insulin peptide is a peptide comprising or derived from B:9-23 peptides or comprising or derived from C-peptide 1-30.

In some embodiments, the immunogenic insulin peptide is derived from an insulin B:9-23 segment or derived from a portion of an insulin B:9-23 segment, is immunogenic, and comprises or is derived from at least a portion of the insulin B chain, an immunogenic mutant thereof, or an immunogenic fragment thereof.

In some embodiments, the immunogenic insulin peptide comprises a peptide selected from or derived from the group consisting of:

FVNQHLCGSH; (SEQ ID NO: 1)

FVNQHLCGSHLVE; (SEQ ID NO: 2)

FVNQHLCGSHLVEALYLVCGERGFFYTPKT; (SEQ ID NO: 3)

FVNQHLcGSHLVEALYLVcGERGFFYTPKT; (SEQ ID NO: 4)

HLVEALY; (SEQ ID NO: 5)

LVEALYLVCGERGFFYTPKT; (SEQ ID NO: 6)

GERGFFYTPK; (SEQ ID NO: 7)

GERGFFYTPKT; (SEQ ID NO: 8)

ERGFFYTPKT; (SEQ ID NO: 9)

GFFYTPKT; (SEQ ID NO: 10)

FFYTPK; (SEQ ID NO: 11)

FFYTPKT; (SEQ ID NO: 12)

REAEDLQVGQVELGGGPGAGSLQPLALEGSLQ; (SEQ ID NO: 13)

EAEDLQVG; (SEQ ID NO: 14)

EAEDLQVGQ; (SEQ ID NO: 15)

EAEDLQVGQVE; (SEQ ID NO: 16)

EAEDLQVGQVEL; (SEQ ID NO: 17)

EAEDLQVGQVELG; (SEQ ID NO: 18)

EAEDLQVGQVELGG; (SEQ ID NO: 19)

FVNQHLcGSHLVEALYLVcGERGFFYTPKT; (SEQ ID NO: 20)

HLVEALY; (SEQ ID NO: 21)

GERGFFYTPKT; (SEQ ID NO: 22)

ERGFFYTPKT; (SEQ ID NO: 23)

GFFYTPKT; (SEQ ID NO: 24)

FFYTPKT; (SEQ ID NO: 25)

REAEDLQVGQVELGGGPGAGSLQPLALEGSLQ; (SEQ ID NO: 26)

EAEDLQVGQ; (SEQ ID NO: 27)

EAEDLQVGQVE; (SEQ ID NO: 28)

EAEDLQVGQVEL; (SEQ ID NO: 29)

YQLENYCN; (SEQ ID NO: 30)

immunogenic portions, mutants, or variants thereof; and/or
combinations thereof.

An aspect of the present disclosure provides for a method of treating or preventing type 1 diabetes (T1D) comprising: administering a therapeutically effective amount of an immunogenic insulin peptide blocking agent to a subject in need thereof, wherein the immunogenic insulin peptide blocking agent inhibits or blocks an interaction of an immunogenic insulin peptide and a leukocyte.

In some embodiments, the immunogenic insulin peptide blocking agent is an antibody against an immunogenic insulin peptide or segment thereof, wherein the antibody neutralizes an interaction between the immunogenic insulin peptide or segment thereof and an autoimmune lymphocyte, wherein the autoimmune lymphocyte causes diabetes.

In some embodiments, the immunogenic insulin peptide blocking agent is an immunogenic insulin peptide-specific antibody generated by immunization with an immunogenic insulin peptide.

In some embodiments, the immunogenic insulin peptide blocking agent is a monoclonal antibody against at least an immunogenic portion of B:1-30, B:9-23, B:12-20, B:13-21, or C:1-30, an immunogenic mutant thereof, or combinations thereof.

In some embodiments, the immunogenic insulin peptide elicits an autoimmune response.

In some embodiments, the immunogenic insulin peptide is a peptide derived from an insulin B chain.

In some embodiments, the immunogenic insulin peptide is a peptide comprising, derived from, or a mutant of at least a portion of B:1-30, B:9-23, B:12-20, or B:13-21.

In some embodiments, the immunogenic insulin peptide is a peptide comprising or derived from B:9-23 peptides or C-peptide 1-30.

In some embodiments, the immunogenic insulin peptide is derived from an insulin B:9-23 segment or derived from a portion of an insulin B:9-23 segment, is immunogenic, and comprises or is derived from at least a portion of the insulin B chain, an immunogenic mutant thereof, or an immunogenic fragment thereof.

In some embodiments, the immunogenic insulin peptide comprises a peptide or is derived from a peptide selected from the group consisting of:

FVNQHLCGSH; (SEQ ID NO: 1)

FVNQHLCGSHLVE; (SEQ ID NO: 2)

FVNQHLCGSHLVEALYLVCGERGFFYTPKT; (SEQ ID NO: 3)

FVNQHLcGSHLVEALYLVcGERGFFYTPKT; (SEQ ID NO: 4)

HLVEALY; (SEQ ID NO: 5)

LVEALYLVCGERGFFYTPKT; (SEQ ID NO: 6)

GERGFFYTPK; (SEQ ID NO: 7)

GERGFFYTPKT; (SEQ ID NO: 8)

ERGFFYTPKT; (SEQ ID NO: 9)

GFFYTPKT; (SEQ ID NO: 10)

-continued

FFYTPK; (SEQ ID NO: 11)

FFYTPKT; (SEQ ID NO: 12)

REAEDLQVGQVELGGGPGAGSLQPLALEGSLQ; (SEQ ID NO: 13)

EAEDLQVG; (SEQ ID NO: 14)

EAEDLQVGQ; (SEQ ID NO: 15)

EAEDLQVGQVE; (SEQ ID NO: 16)

EAEDLQVGQVEL; (SEQ ID NO: 17)

EAEDLQVGQVELG; (SEQ ID NO: 18)

EAEDLQVGQVELGG; (SEQ ID NO: 19)

FVNQHLcGSHLVEALYLVcGERGFFYTPKT; (SEQ ID NO: 20)

HLVEALY; (SEQ ID NO: 21)

GERGFFYTPKT; (SEQ ID NO: 22)

ERGFFYTPKT; (SEQ ID NO: 23)

GFFYTPKT; (SEQ ID NO: 24)

FFYTPKT; (SEQ ID NO: 25)

REAEDLQVGQVELGGGPGAGSLQPLALEGSLQ; (SEQ ID NO: 26)

EAEDLQVGQ; (SEQ ID NO: 27)

EAEDLQVGQVE; (SEQ ID NO: 28)

EAEDLQVGQVEL; (SEQ ID NO: 29)

YQLENYCN; (SEQ ID NO: 30)

immunogenic portions, mutants, or variants thereof; and/or combinations thereof.

Other objects and features will be in part apparent and in part pointed out hereinafter.

DESCRIPTION OF THE DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

DETAILED DESCRIPTION OF THE INVENTION

Figures 1A, 1B, 1C, 1D, 1E, 1F, 1G, 1H, 1I:
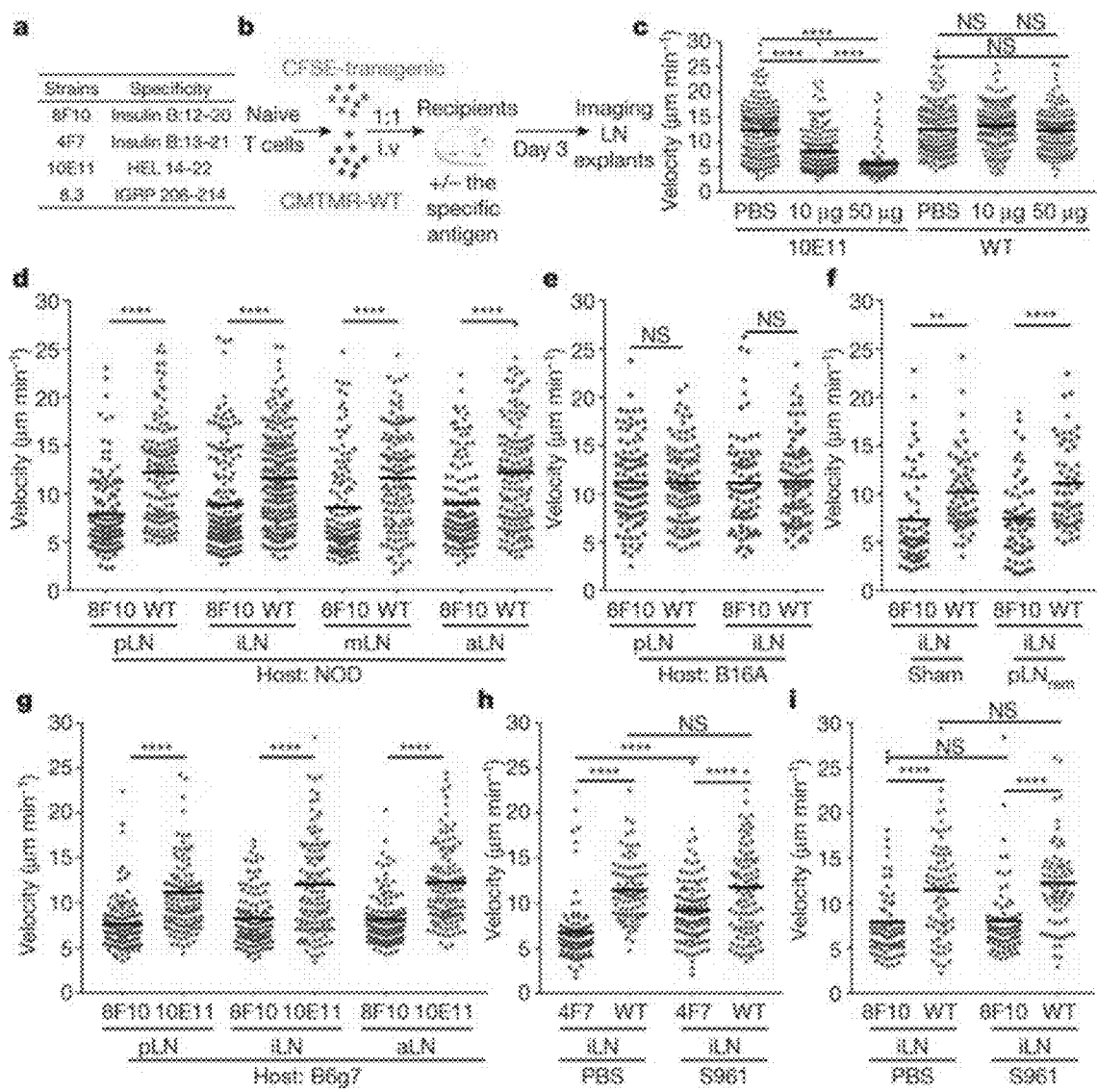
FIG. 1a-FIG. 1i: Peripheral insulin presentation is systemic, epitope-specific, and occurs physiologically. a, Specificities of the antigen-specific T cells. b, The scheme of the transplant and two-photon imaging experiments using CFSE and CMTMR labels for transgenic and wild-type (WT) T cells, respectively. LN, lymph node. c-i, Mean track velocities of: 10E11 and wild-type (WT) CD4 T cells in mice given PBS or the indicated amounts of HEL (c); 8F10 and wild-type CD4 T cells in NOD (d) or B16A (e) mice; 8F10 and wild-type CD4 T cells in NOD mice after surgical removal of the pancreatic lymph nodes ($pLN_{rem}$) or sham surgery (f); 8F10 and 10E11 CD4 T cells in B6g7 mice 24 h after transfer (g); 4F7 and wild-type (h) or 8F10 and wild-type (i) CD4 T cells in NOD mice infused with S961 or PBS. pLN, pancreatic lymph node; iLN, inguinal lymph node; mLN, mesenteric lymph node; aLN, axillary lymph node. Data are pooled results from at least three independent experiments. Each dot represents the velocity of one T cell, and the bar denotes the mean of all T cells in the group. $P<0.001$; **$p<0.0001$; one-way ANOVA with Sidak's multiple comparisons test. NS, not significant.

Here is disclosed methods for detecting, monitoring, and treating Type 1 diabetes (T1D) by detecting and/or targeting peptides that are produced by the pancreas in a subject having T1D.

The present disclosure is based, at least in part, on the discovery and identification of peptides that identify and are responsible for autoimmune [type 1] diabetes. Disclosed herein, is a new approach using mass spectrometry of isolated insulin granules that lead to the identification of insulin peptides involved in T1D. It was also discovered that circulating blood cells after a glucose challenge capture peptides from pancreatic islets. Finding such peptides represents a procedure that can be used as a diagnostic of an ongoing diabetic process.

The present disclosure is also based, at least in part, on the discovery that antibodies to insulin peptides affect the development of autoimmune [type 1] diabetes, representing a new approach targeting specific moieties that initiate autoimmune [type1] diabetes. Disclosed herein, are identified peptides from insulin released from blood-identified in circulating leukocytes. A series of monoclonal antibodies were made to the insulin peptides that neutralize their interaction with the autoimmune lymphocytes that cause diabetes.

The disclosed technology involves the identification of a series of peptides that are produced by the pancreas and initiate T1 D in individuals that are predisposed toward disease. The peptides that elicit an autoimmune response have been identified as deriving from the B chain or a portion of the B chain of insulin particularly the series that encompass B:9-23 peptides and from the C-peptide 1-30.

One aspect of the present disclosure provides for a method of diagnosing/monitoring/prognosing individuals with or at risk of developing T1 D.

Another aspect of the present disclosure provides for methods of treating T1D by blocking the interaction of these peptides with leukocytes or by targeting these leukocytes directly.

The antibody can be to any peptide that interacts with a T1D causing T cell. For example, the antibody can be against any peptide that elicits an autoimmune response, such as those identified as deriving from the B chain of insulin particularly the series that encompasses B:9-23 peptides or from the C:1-30. As another example, the antibodies can be against B:12-20 or B:1-30, which showed attenuation of T1 D. As another example, the antibody can be a monoclonal antibody against B:9-23, B:12-20, B:1-30, or C:1-30, or combinations or immunogenic portions or mutants thereof.

Identification of catabolized insulin peptide fragments containing defined pathogenic epitopes in β-cell granules in mice and humans. Examples of identified peptide epitopes are below.

Human immunogenic peptide sequences from 5K granules:

| SEQ ID NO: | Sequence | Segment | start | end |
|---|---|---|---|---|
| 1 | FVNQHLCGSH | B chain | 1 | 10 |
| 2 | FVNQHLCGSHLVE | B chain | 1 | 13 |
| 3 | FVNQHLCGSHLVEALYLVCGERGFFYTPKT | B chain | 1 | 30 |
| 4 | FVNQHLcGSHLVEALYLVcGERGFFYTPKT | B chain | 1 | 30 |
| 5 | HLVEALY | B chain | 10 | 16 |
| 6 | LVEALYLVC(+119.00)GERGFFYTPKT | B chain | 11 | 30 |
| 7 | GERGFFYTPK | B chain | 20 | 29 |
| 8 | GERGFFYTPKT | B chain | 20 | 30 |
| 9 | ERGFFYTPKT | B chain | 21 | 30 |
| 10 | GFFYTPKT | B chain | 23 | 30 |
| 11 | FFYTPK | B chain | 24 | 29 |
| 12 | FFYTPKT | B chain | 24 | 30 |
| 13 | REAEDLQVGQVELGGGPGAGSLQPLALEGSLQ | C peptide | 1 | 31 |
| 14 | EAEDLQVG | C peptide | 1 | 8 |
| 15 | EAEDLQVGQ | C peptide | 1 | 9 |
| 16 | EAEDLQVGQVE | C peptide | 1 | 11 |
| 17 | EAEDLQVGQVEL | C peptide | 1 | 12 |
| 18 | EAEDLQVGQVELG | C peptide | 1 | 13 |
| 19 | EAEDLQVGQVELGG | C peptide | 1 | 14 |

Human from 5K granules:

| | Sequence | Segment | start | end |
|---|---|---|---|---|
| 20 | FVNQHLcGSHLVEALYLVcGERGFFYTPKT | B chain | 1 | 30 |
| 21 | HLVEALY | B chain | 10 | 16 |
| 22 | GERGFFYTPKT | B chain | 20 | 30 |
| 23 | ERGFFYTPKT | B chain | 21 | 30 |
| 24 | GFFYTPKT | B chain | 23 | 30 |
| 25 | FFYTPKT | B chain | 24 | 30 |
| 26 | REAEDLQVGQVELGGGPGAGSLQPLALEGSLQ | C peptide | 1 | 31 |
| 27 | EAEDLQVGQ | C peptide | 1 | 9 |
| 28 | EAEDLQVGQVE | C peptide | 1 | 11 |
| 29 | EAEDLQVGQVEL | C peptide | 1 | 12 |
| 30 | YQLENYCN | A chain | 13 | 21 |

Formulation

The agents and compositions described herein can be formulated by any conventional manner using one or more pharmaceutically acceptable carriers or excipients as described in, for example, Remington's Pharmaceutical Sciences (A.R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A.R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, subcutaneous, intranasal, epidural, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating type 1 diabetes in a subject in need administration of a therapeutically effective amount of a peptide blocking agent (e.g., immunogenic insulin peptide blocking agent, insulin peptide blocking agent, pancreatic islet peptide blocking agent, leukocyte blocking agent), so as to reduce peptide-leukocyte interaction or reduce peptide-epitope interaction.

Methods described herein are generally performed on a subject in need thereof. A subject in need of the therapeutic methods described herein can be a subject having, diagnosed with, suspected of having, or at risk for developing type 1 diabetes. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans. For example, the subject can be a human subject.

Generally, a safe and effective amount of a peptide blocking agent is, for example, that amount that would cause the desired therapeutic effect in a subject while minimizing undesired side effects. In various embodiments, an effective amount of a peptide blocking agent described herein can substantially inhibit development of diabetes, slow the progress of diabetes, or limit the development of diabetes.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a peptide blocking agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to block the interaction of insulin/pancreatic islet peptides and leukocytes.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a peptide blocking agent can occur as a single event or over a time course of treatment. For example, a peptide blocking agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for diabetes.

A peptide blocking agent can be administered simultaneously or sequentially with another agent, such as an antibiotic, an anti-inflammatory, or another agent. For example, a peptide blocking agent can be administered simultaneously with another agent, such as an antibiotic or an anti-inflammatory. Simultaneous administration can occur through administration of separate compositions, each containing one or more of a peptide blocking agent, an antibiotic, an anti-inflammatory, or another agent. Simultaneous administration can occur through administration of one composition containing two or more of a peptide blocking agent, an antibiotic, an anti-inflammatory, or another agent. A peptide blocking agent can be administered sequentially with an antibiotic, an anti-inflammatory, or another agent. For example, a peptide blocking agent can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening potential drug candidates.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlogP of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlogP of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to peptide blocking agents, antibodies, assays, or reagents. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Pancreatic Islets Communicate with Lymphoid Tissue Via Exocytosis of Immunogenic Insulin Peptides First is the finding by mass spectrometry of the range of insulin catabolic products that are the potential peptides that initiate and perpetuate type 1 diabetes (see e.g., FIGS. 3 and 4). These likely show, for the first time, the real structures of the potential culprits.

Second is the finding that blood cells after a high glucose challenge contain the insulin peptides bound to their histocompatibility [class II] molecules; this indicates that as the beta cell exocytosis insulin and peptides some are bound to the circulating leukocytes—this has never been reported. But the key issue here is that such uptake is blocked by administering monoclonal antibodies to peptides; that is the antibodies neutralize the released peptides and stop them from interacting with the leukocytes.

Abstract

Tissue-specific autoimmunity occurs when selected antigens presented by susceptible alleles of the major histocompatibility complex are recognized by T cells. However, the reason why certain specific self-antigens dominate the response and are indispensable for triggering autoreactivity is unclear. Spontaneous presentation of insulin is essential for initiating autoimmune type 1 diabetes in non-obese diabetic mice[1,2]. A major set of pathogenic CD4 T cells specifically recognizes the 12-20 segment of the insulin B-chain (B:12-20), an epitope that is generated from direct presentation of insulin peptides by antigen-presenting cells[3,4]. These T cells do not respond to antigen-presenting cells that have taken up insulin that, after processing, leads to presentation of a different segment representing a one-residue shift, B:13-21[4]. CD4 T cells that recognize B:12-20 escape negative selection in the thymus and cause diabetes, whereas those that recognize B:13-21 have only a minor role in autoimmunity[3,4,5]. Although presentation of B:12-20 is evident in the islets[3,6], insulin-specific germinal centres can be formed in various lymphoid tissues, suggesting that insulin presentation is widespread[7,8]. Here we use live imaging to document the distribution of insulin recognition by CD4 T cells throughout various lymph nodes. Furthermore, we identify catabolized insulin peptide fragments containing defined pathogenic epitopes in β-cell granules from mice and humans. Upon glucose challenge, these fragments are released into the circulation and are recognized by CD4 T cells, leading to an activation state that results in transcriptional reprogramming and enhanced diabetogenicity. Therefore, a tissue such as pancreatic islets, by releasing catabolized products, imposes a constant threat to self-tolerance. These findings reveal a self-recognition pathway underlying a primary autoantigen and provide a foundation for assessing antigenic targets that precipitate pathogenic outcomes by systemically sensitizing lymphoid tissues.

Main

Figures 5A, 5B, 5C, 5D, 5E, 5F, 5G, 5H, 5I, 5J, 5K, 5L:
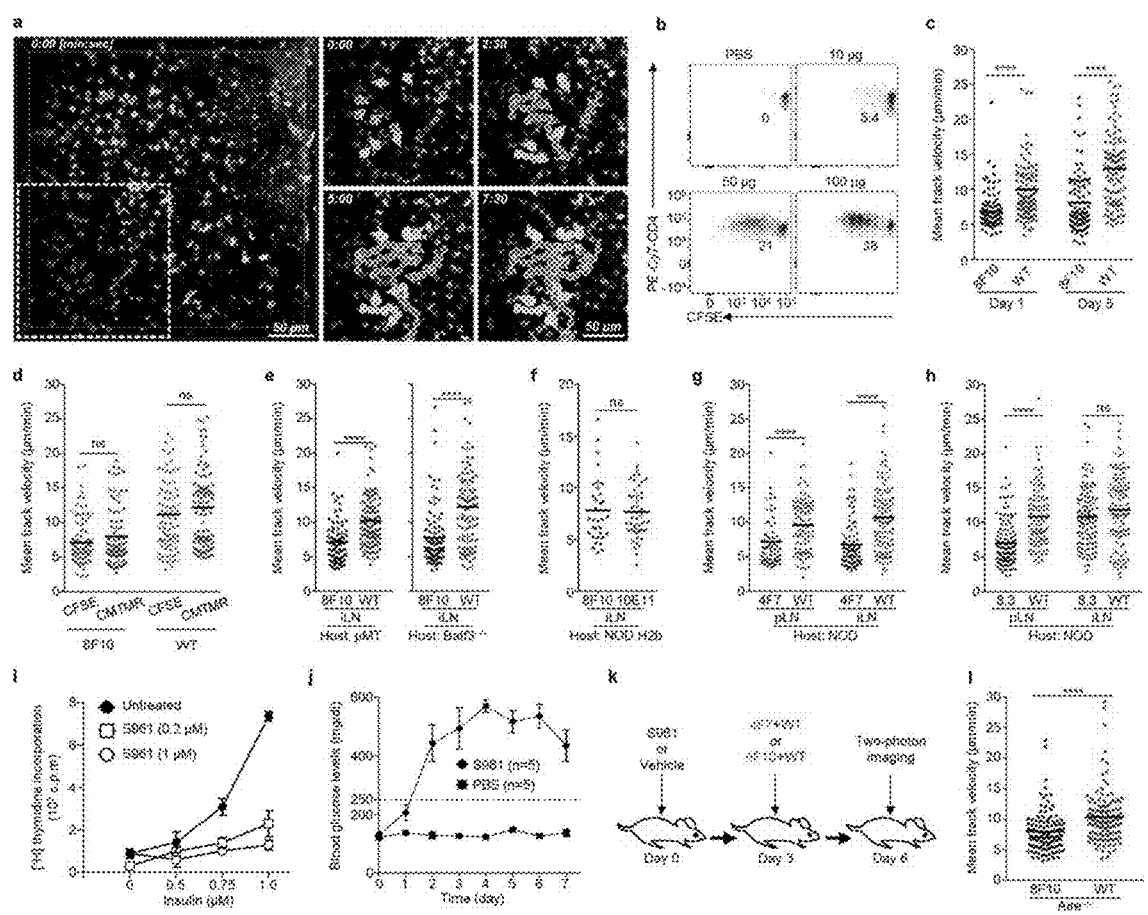
FIG. 5a-FIG. 5l: Probing peripheral antigen presentation by two-photon imaging; the motility assay. a, Representative 3D reconstructions of two-photon z-stacks visualizing CFSE-labelled anti-HEL 10E11 TCR transgenic and CMTMR-labelled wild-type CD4 T cells in an iLN explant on day 3 post transfer. Individual T cells were tracked in the area bound by the dashed line. Right, magnified views of this region, showing movement of T cells over a 7.5-min time interval. Quantification was performed over a 5-min interval. Cyan and purple tracks represent 10E11 and wild-type T cells, respectively. Mice were injected with 10 μg HEL. b, NOD mice (CD45.1) were injected intraperitoneally with indicated amounts of HEL. Six hours after injection, naive CFSE-labelled 10E11 (CD45.2) T cells were transferred. On day 3, CFSE dilution of the transferred T cells (CD45.2+ CD45.1$^-$CD4$^+$Vβ8.1/8.2$^+$) in the iLNs was measured by flow cytometry. Data are representative of two independent experiments. c, Mean track velocities of 8F10 and wild-type CD4 T cells in iLNs from NOD recipients on day 1 or day 5 post transfer. d, CFSE(8F10) plus CMTMR(WT) or CMTMR(8F10) plus CFSE(WT) T cells were separately transferred into two cohorts of NOD recipients, and their mean track velocities in iLNs on day 3 were compared by paired two-photon imaging analysis. e, Mean track velocities of 8F10 and wild-type CD4 T cells in NOD.μMT or NOD.Batf3$^{-/-}$ recipients on day 3 post transfer. f, Mean track velocities of 8F10 and 10E11 T cells in NOD.H2b recipients 24 h post transfer. g, h, Mean track velocities of 4F7 and wild-type CD4 (g) or 8.3 and wild-type CD8 (h) T cells in NOD recipients on day 3 post transfer. i, Response (mean±s.e.m.) of the B:13-21-specific IIT-3 T cells to ConA-activated peritoneal macrophages treated with or without S961 before insulin pulse. j, Blood glucose levels (mean±s.e.m.) of 3-week old NOD mice infused with S961 or PBS via osmotic pumps. k, The scheme of the experiments in FIG. 1h, i. l, Mean track velocities of 8F10 and wild-type CD4 T cells in iLNs of Aire$^{-/-}$ recipients. Data summarize two (c, d, f, l) or three (e, g, h) independent experiments. Each dot represents individual T cell tracks, and the bar denotes the mean. ns, not significant; ****P<0.0001; one-way ANOVA with Sidak's multiple comparisons test (c, d, g, h) or two-tailed unpaired Student's t-test (e, f, l).

On the basis of previous studies demonstrating constrained T-cell migration during limited antigen recognition[9,10,11,12], we investigated insulin presentation in peripheral lymph nodes by two-photon microscopy of lymph-node explants following transfer of insulin-specific T cells (FIG. 1a). These were transferred together with wild-type CD4 T cells as a control; each population of transferred cells was labelled with a different fluorescent probe (FIG. 1b). We monitored the individual trajectories of transplanted T cells within the same region of the lymph nodes and quantified their motility (FIG. 5a). We first performed this assay with a control CD4 T cell (10E11), which recognizes hen egg lysozyme (HEL). These experiments confirm that limited antigen recognition that is insufficient to trigger cell division can be detected by a decrease in the mean velocity of T cells (FIG. 1c, FIG. 5b).

Widespread presentation of insulin peptides was demonstrated by reduced motility of the B:12-20-specific 8F10 T cells in the pancreatic (pLN), inguinal (iLN), mesenteric (mLN) and axillary (aLN) lymph nodes of non-obese diabetic (NOD) mice, relative to wild-type CD4 T cells (FIG. 1d). Motility was reduced to a similar degree on day 1 or day 5 of imaging (FIG. 5c), and was unaffected by switching the labelling of the fluorescent probes (FIG. 5d). The diffuse, rather than clustered, pattern of motility arrest indicates that presentation of insulin peptides was limiting and was not restricted to selected antigen-presenting cells (APCs). Motility of 8F10 T cells was also reduced in pMT and Batf3$^{-/-}$ mice, which are deficient in B cells and XCR1$^+$ dendritic cells, respectively (FIG. 5e).

We performed three experiments to interrogate key parameters of antigen recognition by 8F10 T cells. First, we examined B16A mice, which are deficient in both Ins1 and Ins2 but express a proinsulin transgene with a Tyr16Ala substitution in the B chain[1]. This mutant insulin is bioactive but is not immunogenic to B:12-20- or B:13-21-specific T cells. There was no reduction in motility of 8F10 T cells in the B16A mouse recipients, demonstrating that the effects on T cell motility require specific epitope recognition by the 8F10 T cells (FIG. 1e). Second, we investigated whether prior recirculation through the pLN was required for insulin recognition in other sites. Surgical removal of pLNs did not influence the motility arrest of 8F10 T cells in the iLNs (FIG. 1f). Third, we detected motility arrest of 8F10 T cells in diabetes-resistant B6 mice harbouring the I-A$^{g7}$ haplotype (B6g7) (FIG. 1g) but not in NOD mice with the H2b haplotype (FIG. 5f). Therefore, peripheral insulin presentation to 8F10 T cells requires I-A$^{g7}$ and is not restricted to the NOD strain.

The motility of 4F7 T cells, which specifically recognize the B:13-21 epitope, was also markedly reduced in the pLNs and iLNs of NOD recipients (FIG. 5g). By contrast, the 8.3 CD8 T cells, which recognize the islet-specific glucose-6-phosphatase-related protein (IGRP[13], a protein that is expressed in the endoplasmic reticulum of β-cells), exhibited reduced motility in the pLN but not in the iLN (FIG. 5h). Therefore, epitopes of insulin, but not those from IGRP, a cell-associated antigen, are systemically available.

We hypothesized that presentation of the low concentrations of circulating insulin (about 40 pM) might require insulin receptor-mediated uptake by APCs. To test this, we examined the effects of S961, an insulin receptor antagonist[14]. In assays on cultured cells, S961 impaired the ability of concanavalin A (ConA)-activated macrophages to present insulin (FIG. 5i). In vivo blockade of insulin receptor by infusion of mice with S961 via osmotic pump caused a sustained increase in blood glucose levels (FIG. 5j), permitting two-photon microscopy analysis (FIG. 5k). A significant reduction in mean velocity of transferred 4F7 T cells was observed in lymph nodes of control mice infused with phosphate-buffered saline (PBS) (FIG. 1h). Although the motility of 4F7 T cells was also arrested after S961 infusion, the magnitude of the reduction was significantly smaller than with PBS (FIG. 1h). Therefore, blockade of insulin receptor-mediated uptake of insulin partially abrogated recognition by the 4F7 T cells, suggesting that free insulin peptides are an additional source of the B:13-21 epitope. By contrast, the motility arrest of 8F10 T cells remained at a comparable level in recipients infused with PBS or S961 (FIG. 1i), indicating that the presence of B:12-20 is independent of insulin receptor-mediated uptake of insulin. This epitope must therefore derive from insulin peptides that reach the peripheral lymphoid organs. Of note, APCs expressing autoimmune regulator (AIRE)[15] are not a major source of insulin peptides (FIG. 5l).

Figures 6A, 6B, 6C, 6D, 6E:
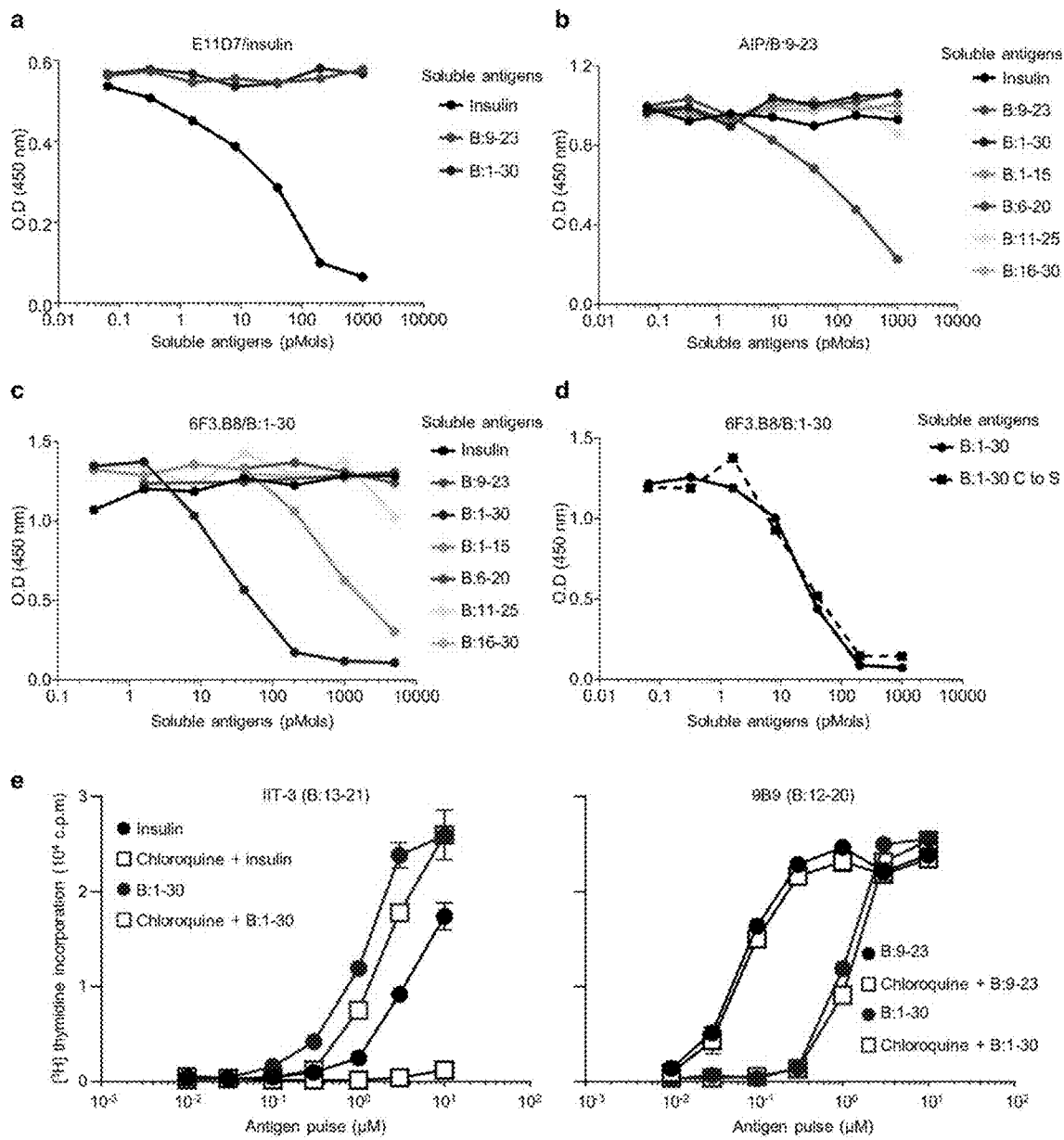
FIG. 6a-FIG. 6e: Analysis of insulin peptide-specific monoclonal antibodies and presentation of the intact B-chain. a-c, Competitive ELISA responses showing the binding of: anti-insulin monoclonal antibody (E11D7) to plate-bound insulin (a) anti-B:9-23 monoclonal antibody (AIP) to plate-bound B:9-23 (b), and anti-B:1-30 monoclonal antibody (6F3.B8) to plate-bound B:1-30 (c) in the presence of serial dilutions of the indicated soluble antigens as a competitive inhibitor. Inhibition by a specific soluble antigen indicates the specificity of the monoclonal antibody to this antigen. d, Competitive ELISA responses showing the binding of 6F3.B8 to plate-bound B:1-30 in the presence of soluble unmodified B:1-30 or B:1-30 in which the two cysteines were changed to serines (B:1-30 C to S). The results indicate the intrachain link formed by the cysteines does not influence the specificity of the 6F3.B8 monoclonal antibody. Data are means representing two independent experiments. e, Responses of the B:13-21-specific IIT-3 (left) or the B:12-20-specific 9B9 (right) T cell hybridoma to C3g7 APCs treated with or without 100 μM chloroquine for 2 h and pulsed with indicated antigens after extensive washes. C3g7 cells are a B cell lymphoma line expressing I-A$^{g7}$, and are used as APCs. The results of the effects of chloroquine indicate that reactivity to insulin, but not to B:9-23 or B:1-30 require internal processing. Data are mean±s.e.m., representative of two independent experiments.

We identified insulin peptides in β-cell granules using peptide-specific monoclonal antibodies and mass spectrometry analysis. We used the monoclonal antibody AIP, which is specific for B:9-23[3,6], and generated a new monoclonal antibody (clone 6F3.B8) by immunization with the entire insulin B-chain (B:1-30). The two antibodies were not cross-reactive and neither recognized native insulin (FIG. 6a-d). Notably, presentation of B:1-30 activated insulin-reactive T cells without the need for internal processing (FIG. 6e).

Figures 2A, 2B, 2C, 2D, 2E, 2F, 2G, 2H:
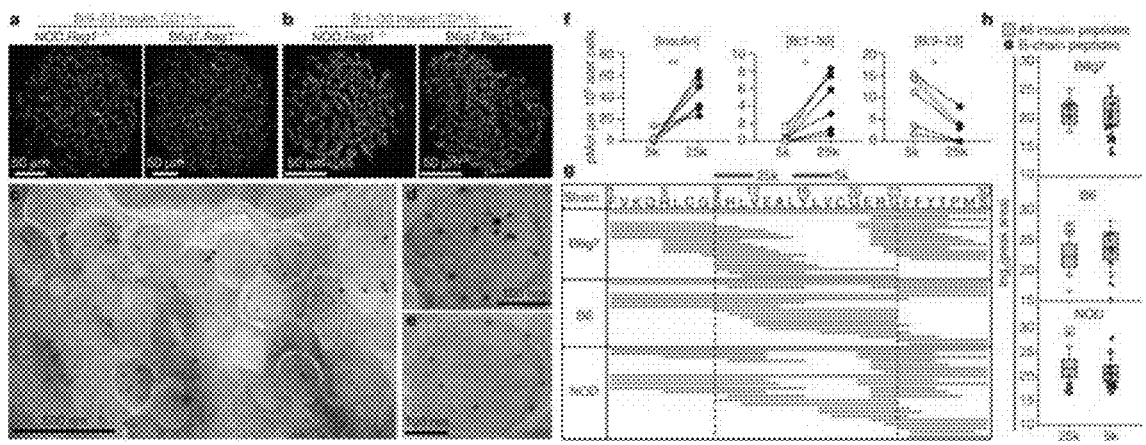
FIG. 2a-FIG. 2h: Generation of insulin peptides in β-cell granules. a, b, Immunofluorescence of isolated islets stained for B:9-23 (a) or B:1-30 (b), CD11c and insulin. Data are representative of 50 islets per group in three independent experiments. c, Immunogold electron microscopy showing antibodies against B:1-30 (large gold) and insulin (small gold) in a representative β-cell. d, e, A representative granule that contains both B:1-30 and insulin (d) or insulin only (e) is shown. The arrowhead in d indicates the B:1-30 peptide. Data are representative of 317 granules analyzed in three independent experiments. f, Competitive ELISA showing quantification of insulin, B:1-30 and B:9-23 in granules isolated by centrifugation of islets from B6g7 mice at 5,000 g (5 k) or 25,000 g (25 k). Each line represents one paired experiment using 4-8 mice. *$P<0.05$; **$P<0.01$; two-tailed paired Student's t-test. g, Peptide coverage of insulin B chain by sequences identified in 25 k (red) and 5 k (blue) β-cell granules using nLC-MS/MS analysis. Each line represents the alignment of individual peptides with insulin-2 B:1-30. Data are from four independent analyses using islets from 8-10 mice per strain. h, Box plot of $\log_2$ (mass spectrometry peak area), showing the abundance of individual insulin B-chain peptides (purple) in the 25 k and 5 k granules relative to all insulin peptides, including the C-peptides (box). Boxes with dashed outlines denote B:1-30 with a high abundance. Box plots show the median, box edges represent the first and third quartiles, and the whiskers extend to 1.5× interquartile range.

We previously identified B:9-23 in a set of LAMP1-positive vesicles in β-cells[3]. These vesicles are distinct from insulin-containing dense core granules and can be separated from them by differential centrifugation[6]. They are consistent with the crinophagic bodies that result from fusion of the dense core granules to lysosomes[16,17,18], and contain peptides that preferentially stimulate 8F10 T cells[6]. Immunofluorescence with AIP showed a punctate pattern of B:9-23 staining in β-cells from NOD.Rag1$^{-/-}$ or B6g7.Rag1$^{-/-}$ mice (FIG. 2a). By contrast, B:1-30 staining using 6F3.B8 was more diffuse in nearly all the β-cells and co-stained with insulin (FIG. 2b). Using double immunogold-labelling antibodies, we detected B:1-30 in granules containing insulin (FIG. 2c). Many granules (106 out of 317, 33%) contained both B:1-30 and insulin (FIG. 2d), and the rest contained only insulin (FIG. 2e). AIP did not stain islets satisfactorily after labelling with immunogold.

Regular secretory granules obtained by centrifugation at 25,000 g (25 k) contained significantly higher amounts of insulin than the fraction obtained at 5,000 g (5 k), which includes the crinophagic bodies (FIG. 2f). B:1-30 was primarily found in the 25 k fraction and not in the 5 k fraction, but in concentrations about one tenth that of insulin (FIG. 2f). By contrast, B:9-23 was significantly more abundant in the granules in the 5 k fraction (FIG. 2f).

Figure 7A:
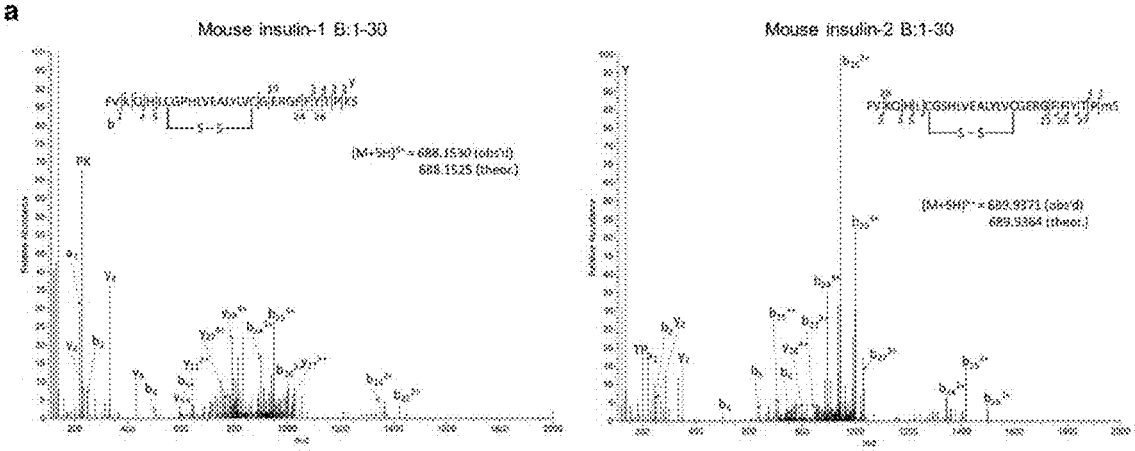
FIG. 7a-FIG. 7c: nLC-MS/MS analysis of mouse β-cell granules. a, Mass spectra of mouse insulin-1 B:1-30 with intramolecular disulphide bonds (left) and mouse insulin-2 B:1-30 with oxidized methionine in position 29 (right). b, Mass spectra of mouse insulin B:9-23 (left) and B:11-23 (right), which were exclusively identified in the 5 k granules of B6g7, B6 and NOD mice. c, Mass spectra of two hybrid peptides identified in the 5 k granules. The sequence (EVEDTPVRSGSNPQM (SEQ ID NO: 31), left) represents a C-peptide (underlined)-islet amyloid polypeptide (IAPP) fusion, and the sequence (EVEDPQVAEVARQ (SEQ ID NO: 32), right) represents a fusion of the N terminus of insulin-2 C-peptide (underlined) with the C terminus of insulin-1 C-peptide.
Figure 7B:
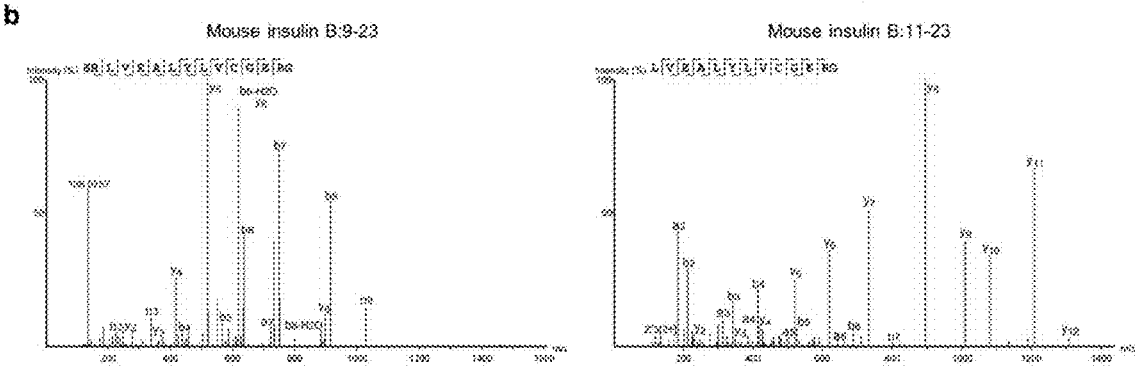
Figure 7C:
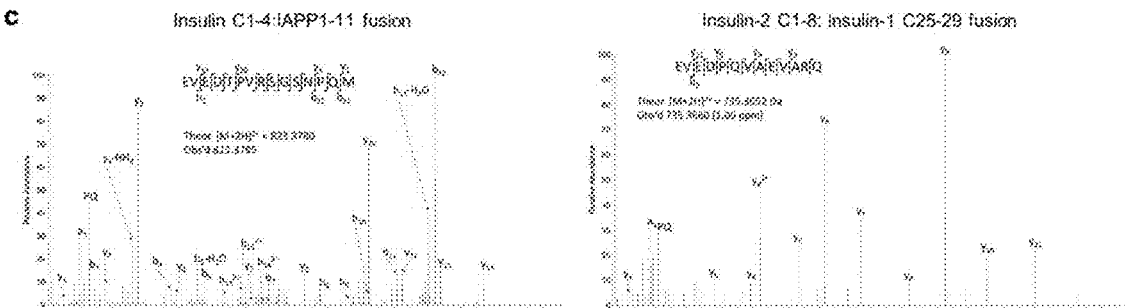

We analyzed the peptidomes of granules prepared from B6g7 mice, B6 mice or 3-week old female NOD mice, by nanoflow liquid chromatography-tandem mass spectrometry (nLC-MS/MS). In all three strains, granules from the 25 k fraction mostly contained sequences from the insulin C-peptide, the intact B:1-30, and a few small peptides from the B chain (FIG. 2g, h, FIG. 7a). By contrast, the granules from the 5 k fraction, contained more diverse short sequences from throughout the B chain (FIG. 2g, h). Peptides derived from the 9-23 region, such as B:9-23 and B:11-23 (FIG. 7b), were identified exclusively in the 5 k granules of all three mouse strains. Manual interrogation of unassigned spectra only identified two putative hybrid peptides in the 5 k granules (FIG. 7c), a C-peptide-islet amyloid polypeptide (IAPP) fusion, and a fusion of the N terminus of the C-peptide of insulin-2 and the C terminus of the C-peptide of insulin-1. Peptides from other proteins were present at much lower levels in comparison to those from insulin.

Figure 8A:
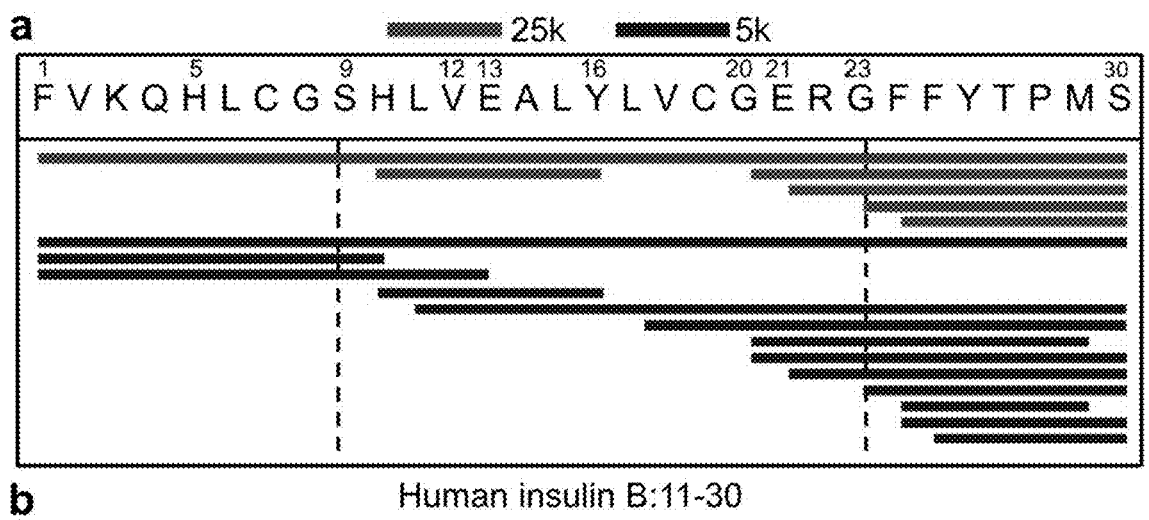
FIG. 8a-FIG. 8b: nLC-MS/MS analysis of human β-cell granules. a, Peptide coverage of insulin B chain identified in human 25 k (red) and 5 k (blue) β-cell granules using nLC-MS/MS analysis. Shown is the alignment of individual peptides (each line) with the human insulin B:1-30 segment. Data summarizes results from four independent runs using human islets from three individual donors. b, A mass spectrum showing a sequence representing human insulin B:11-30 that was identified in the 5 k granules. The cysteinylation in position 19 is indicated.
Figure 8B:
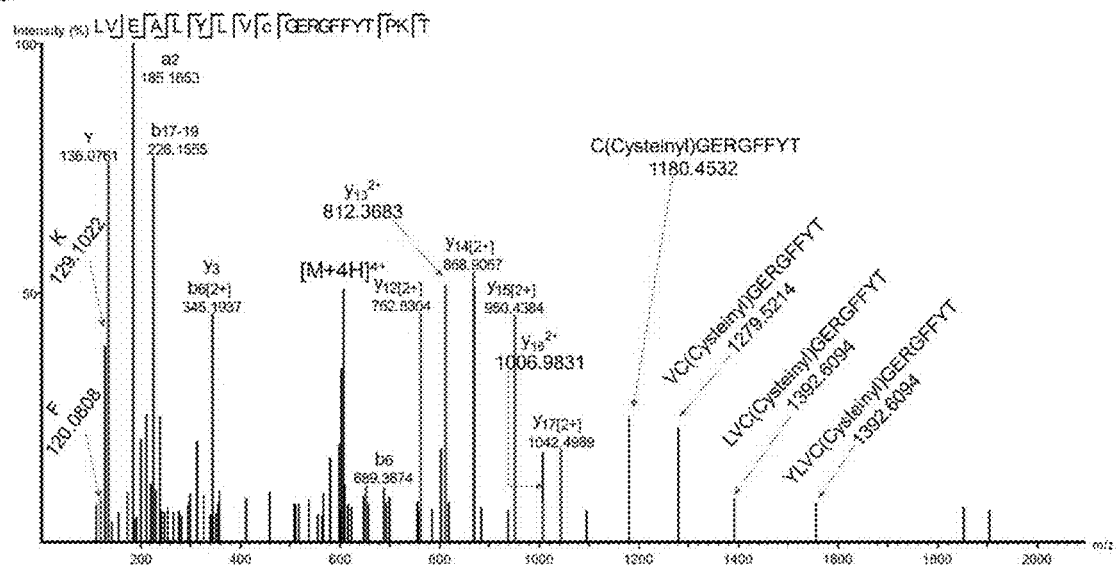

Examination of β-cell granules from human islets revealed a striking similarity in the segregation of peptides between 5 k and 25 k fractions to that from the mouse islets (FIG. 8a). The human 25 k granules contained the intact B chain and a limited number of short sequences. The 5 k fraction contained many short peptides, including a sequence representing B:11-30 (FIG. 8b), containing the HLA(DQ8)-binding B:11-23 determinant, which is recognized by peripheral T cells in patients with type 1 diabetes[19].

Figures 3A, 3B, 3C, 3D, 3E, 3F, 3G:
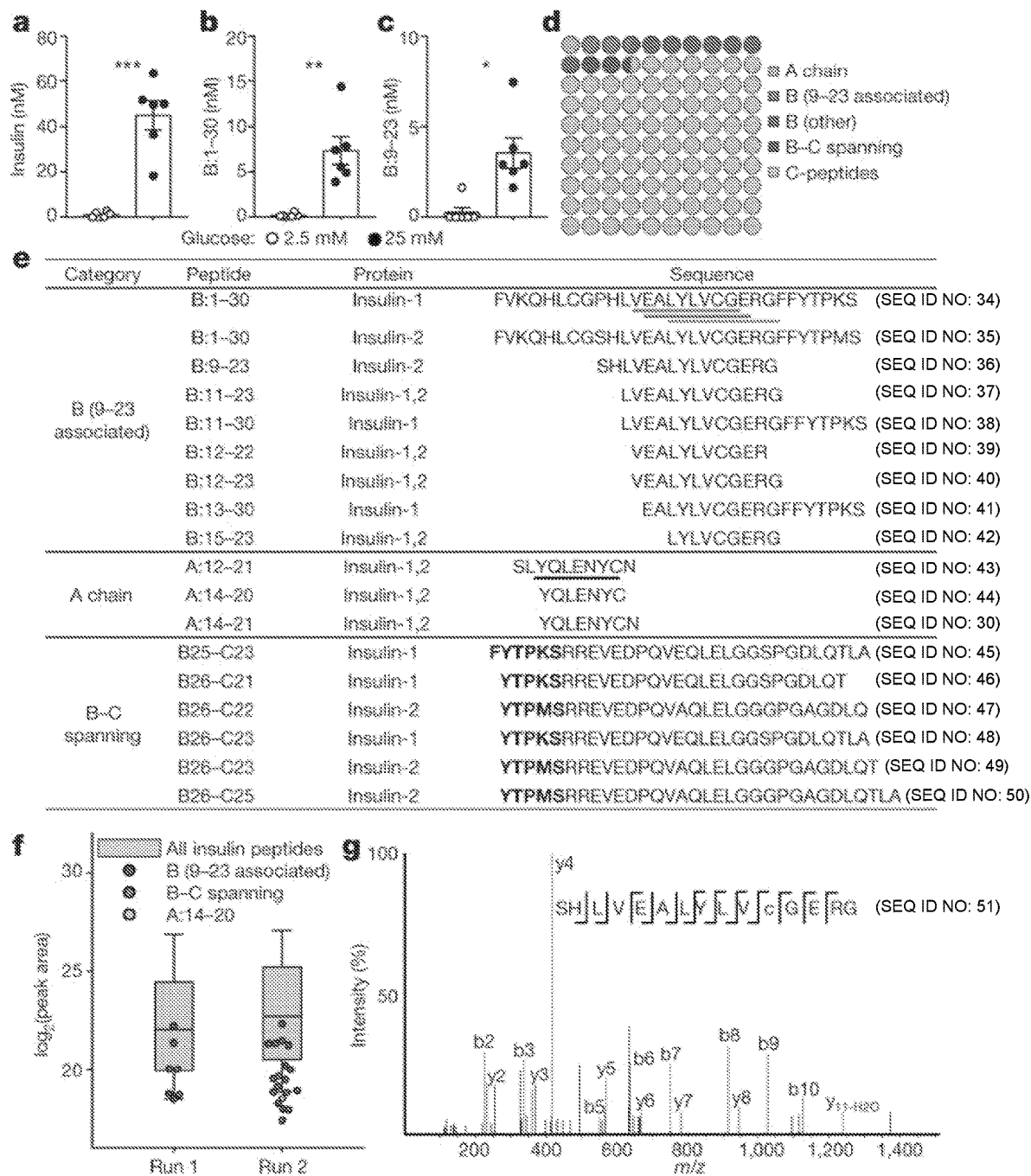
FIG. 3a-FIG. 3g: Secretion of insulin peptides into the circulation upon glucose stimulation. a-c, Insulin (a), B:1-30 (b) and B:9-23 (c) secreted from islets of B6g7 mice during one hour after stimulation with 2.5 mM or 25 mM glucose, quantified by competitive ELISA. Each point represents an independent experiment. *$P<0.05$; $P<0.01$; *$P<0.005$; two-tailed paired Student's t-test. d, A 10×10 dot plot representing the coverage of insulin peptide sequences identified by nLC-MS/MS in supernatants of cultured islets stimulated with 25 mM glucose. Each dot represents 1% coverage of the total. e, Summary of selected insulin peptides containing defined immunogenic epitopes. The following epitopes are underlined: B:12-20 (red), B:13-21 (blue), B:15-23 (green) and A:14-20 (black). In B-C-spanning peptides, the residues of the B chain are shown in bold. f, Box plot of $\log_2$ (peak area) showing abundance of individual B:9-23-associated peptides (blue), B-C-spanning peptides (red) and the A:14-20 peptide (cyan) relative to all insulin peptides (box). Box plots show the median, box edges represent the first and third quartiles, and the whiskers extend to 1.5× interquartile range. g, The mass spectrum of a peptide sequence identified in mouse urine that contains all residues of the insulin B:9-23 peptide, with oxidation of cysteine to cysteic acid (c).
Figures 9A, 9B, 9C, 9D, 9E:
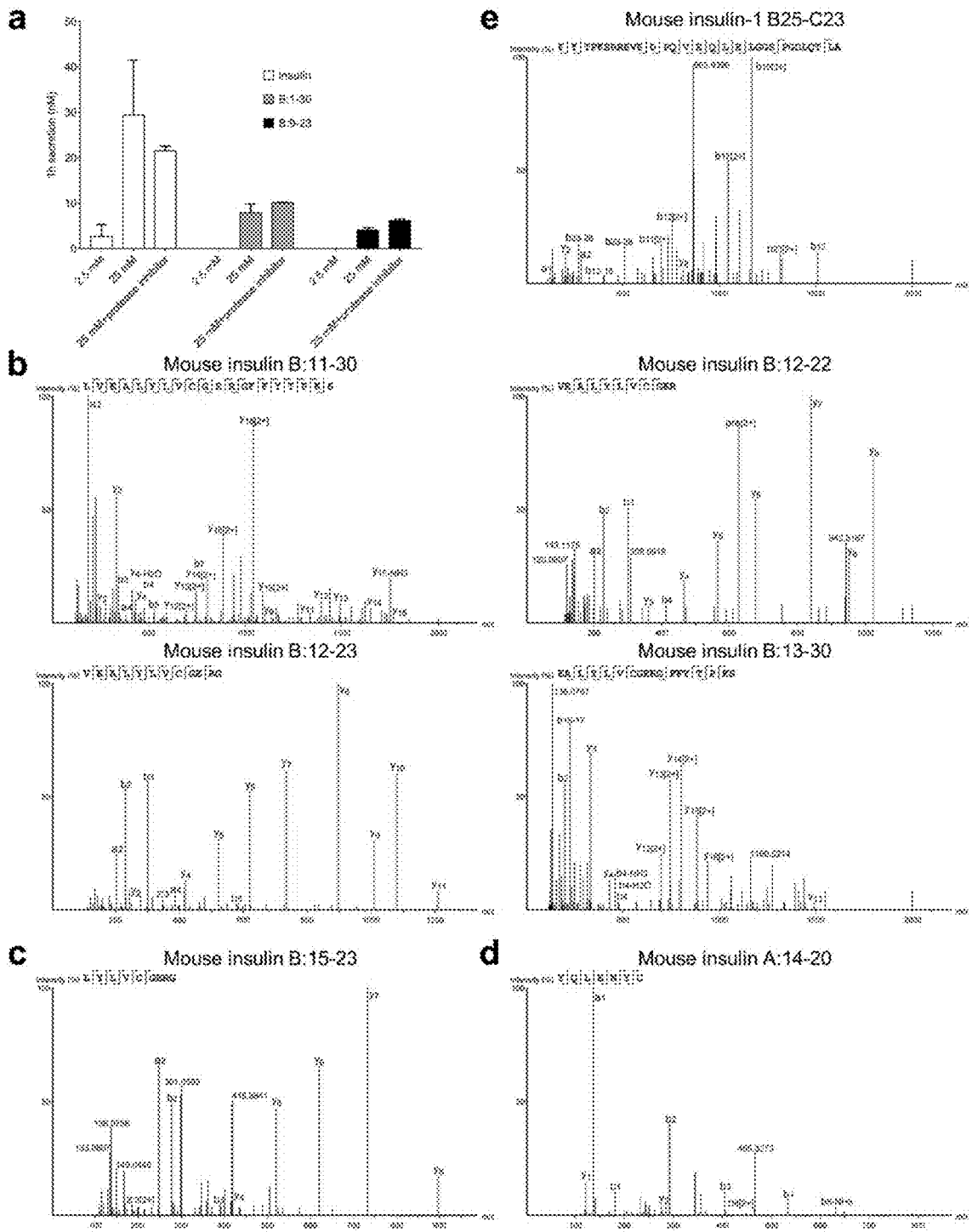
FIG. 9a-FIG. 9e: Analysis of insulin peptides secreted from islets upon glucose challenge. a, Insulin secretion assay was performed as described in FIG. 3a-c, except that protease inhibitors were added during the 25-mM glucose challenge. The supernatants were then collected for the competitive ELISA assay. Data are mean±s.e.m. from two independent experiments. b, Mass spectra of four secreted peptides that contain the B:12-20 and/or B:13-21 epitopes as listed in FIG. 3e. Secreted B:1-30 sequences are identical to those in FIG. 7a, and B:9-23 and B:11-23 share identical sequences with those in FIG. 7b. c, A mass spectrum of the secreted insulin B:15-23 MHC-I (K$^d$)-binding peptide. d, A mass spectrum of the secreted insulin A:14-20 MHC-I (D$^b$)-binding peptide. e, A mass spectrum showing a representative B-C-spanning peptide (B25-C23).

Islets stimulated with 25 mM glucose secreted insulin (FIG. 3a) along with lower concentrations of peptides that were recognized by 6F3.B8 (FIG. 3b) or AIP (FIG. 3c). Secretion of insulin or insulin peptides was not affected when glucose challenge was carried out in the presence of protease inhibitors (FIG. 9a), indicating that the peptides were not generated extracellularly.

Figure 10:
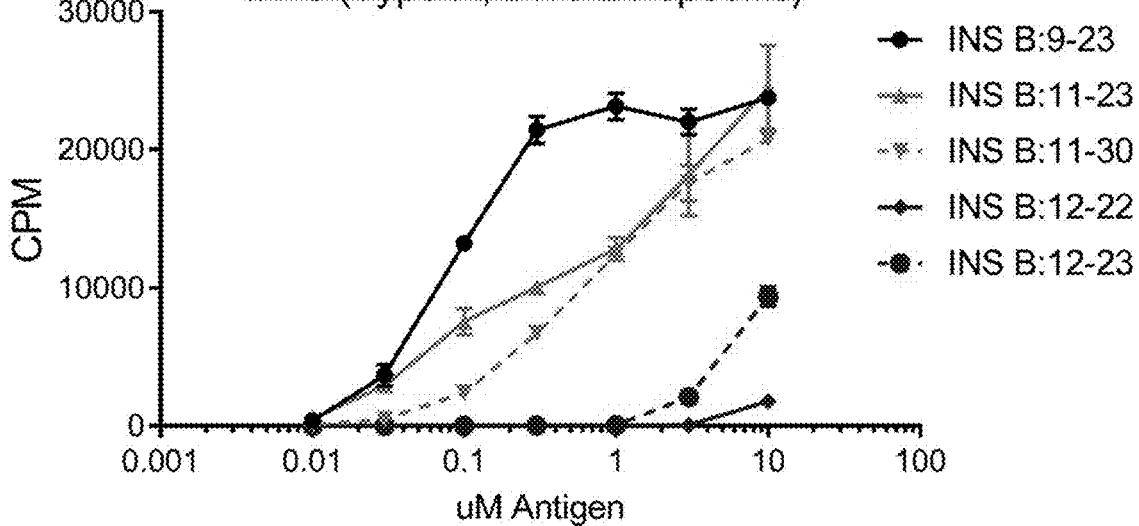
FIG. 10: T cell responses to B:9-23-associated peptides. Responses of three insulin-reactive T cell hybridomas to insulin peptides associated with the 9-23 region of the B chain as identified in FIG. 3e. The C3g7 cells were used as APCs. Data are mean±s.e.m.
Figure 10:
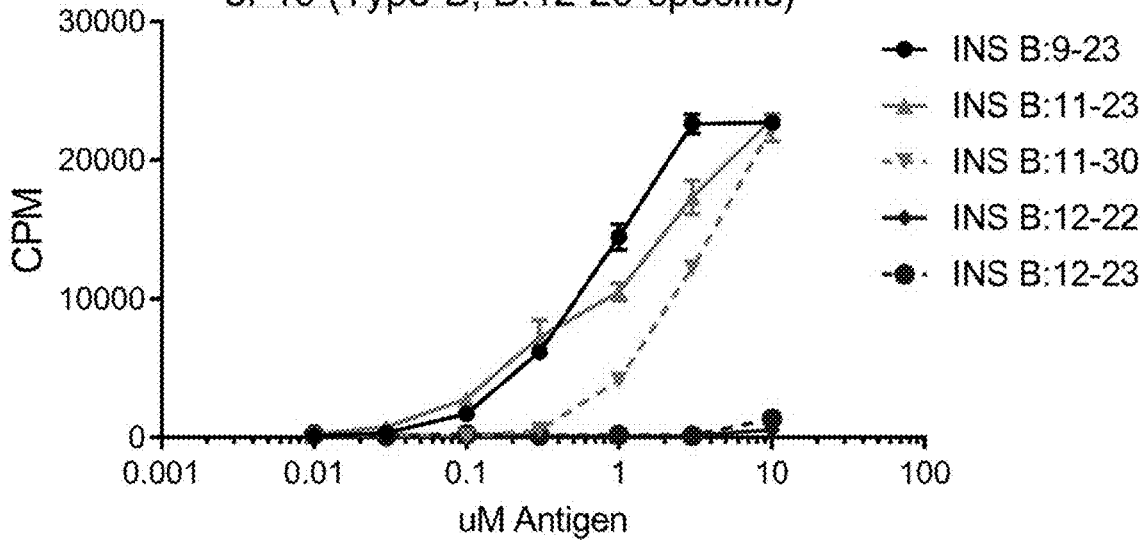
Figure 10:
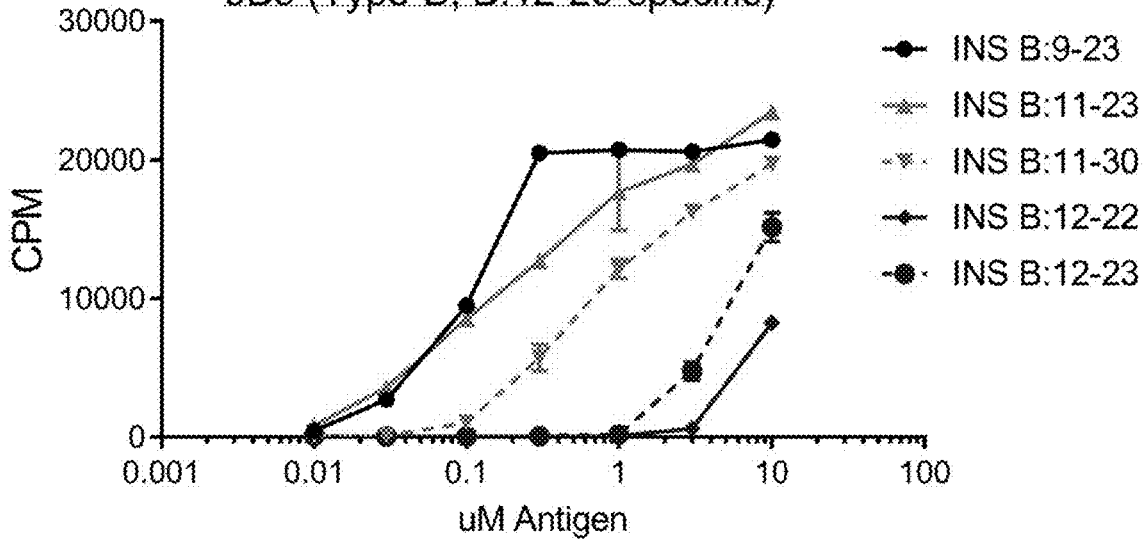

We characterized insulin peptides secreted by β-cells using nLC-MS/MS. Most of these peptides were derived from the C-peptide, along with B-chain-derived sequences related to the 9-23 region and spanning the B-chain—C-peptide (B-C) junction (FIG. 3d). Many of the peptides were identical to or contained pathogenic epitopes that were identified using diabetogenic T cells as probes[1,3,4,20,21,22] (FIG. 3e, FIG. 9b-e). The intact B chain contained identical sequences to peptides identified in the 252 k granules, whereas B:9-23 and B:11-23 were identical to peptides in the 5 k granules (FIG. 3e). Synthetic versions of peptides associated with B:9-23 activated T cells specific for B:12-20 as well as those specific for B:13-21 (FIG. 10). In general, these potentially immunogenic peptides were present at low relative abundance (FIG. 3f).

Figures 11A, 11B, 11C:
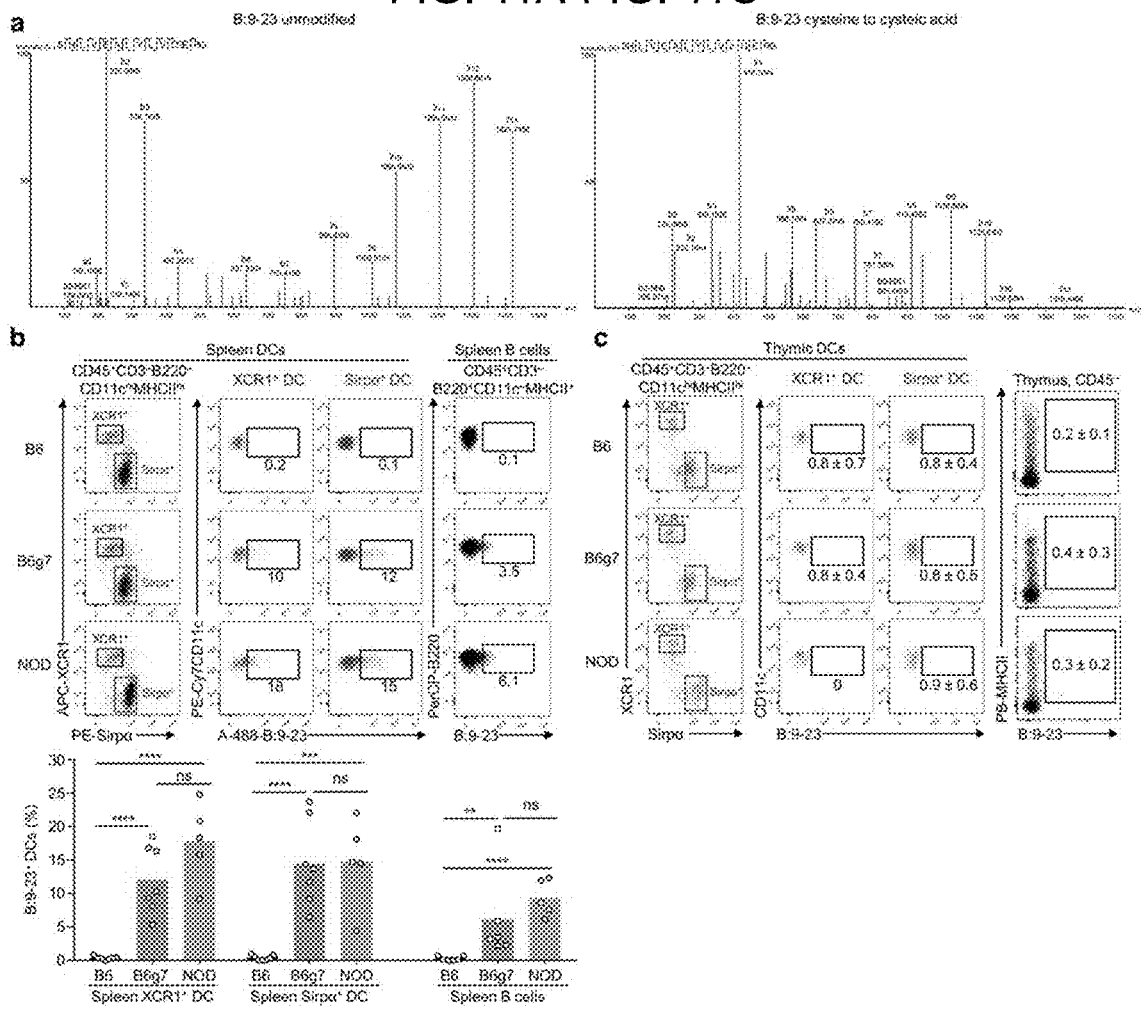
FIG. 11a-FIG. 11c: Characterization of circulating B:9-23 and its localization into lymphoid organs. a, Unmodified synthetic B:9-23 (3 pmol) was spiked into 1 ml PBS, purified using C18 tips, lyophilized, and analyzed by nLC-MS/MS. The data show the appearance of unmodified B:9-23 (left) together with oxidation of Cys19 to cysteic acid (right). b, c, Alexa Fluor 488-conjugated B:9-23 peptide (100 µg) was injected intravenously into 4-week old B6, B6g7 and NOD mice. An hour later, spleens and thymi were harvested, digested with liberase and DNase, and binding to splenic and thymic APCs was measured by flow cytometry. b, Representative FACS plots showing the binding of B:9-23 to splenic XCR1$^+$ and Sirpα$^+$ dendritic cell (DC) subsets and B cells (top). The bar graph summarizes cumulative results from individual mice (each point), pooled from three independent experiments. ns, not significant; $P<0.05$; *$P<0.01$; ****$P<0.005$, two-tailed unpaired Student's t-test. c, Representative FACS plots showing the binding of B:9-23 to thymic XCR1$^+$ and Sirpα$^+$ DC subsets and to CD45$^-$ cells expressing MHCII. Data are mean±S.D from five individual mice per strain from two independent experiments.

We identified a form of B:9-23 containing cysteine oxidized to cysteic acid in mouse urine using antibody capture (FIG. 3g); this is a modification that can occur during sample preparation (FIG. 11a). This finding indicates that B:9-23 is present in the circulation. Indeed, fluorochrome-labelled B:9-23 was rapidly displayed by I-A$^{g7}$-expressing APCs in spleen but not in thymus following intravenous injection (FIG. 11b, c).

Figures 4A, 4B, 4C, 4D, 4E, 4F:
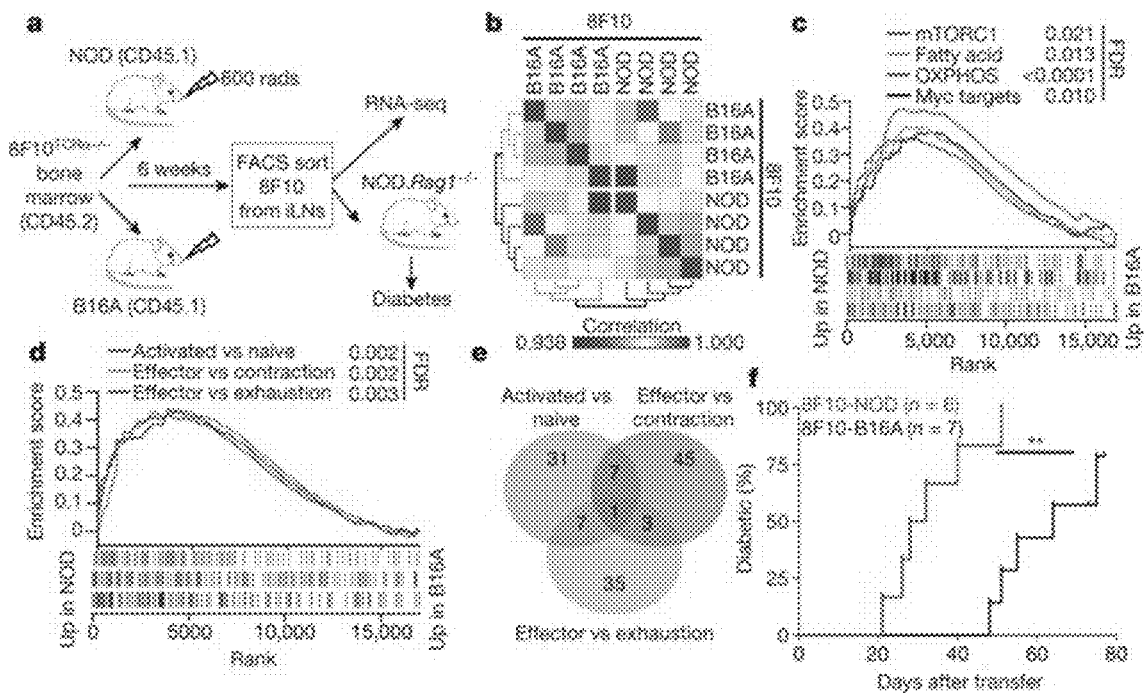
FIG. 4a-FIG. 4f: Acquisition of an effector-like phenotype by 8F10 T cells during antigen recognition. a, Experimental design for b-f. b, Pearson's correlation matrix showing hierarchical clustering of RNA-seq of 8F10 T cells sourced from NOD or B16A hosts. c, GSEA enrichment plots showing a significant correlation (determined by false discovery rate (FDR) Q<0.05) of genes upregulated in the 8F10-NOD samples with four hallmark datasets associated with metabolism pathways. d, GSEA enrichment plots showing a significant correlation of genes upregulated in the 8F10-NOD samples with three immunological signature datasets depicting T cell activation and effector function. e, A Venn diagram showing the number of overlapping genes among the three gene sets in d. f, Incidence of diabetes in NOD.Rag1$^{-/-}$ recipients adoptively transferred with 8F10 T cells isolated from the iLNs of NOD or B16A mice six weeks after bone marrow transfer. **P<0.005; log-rank test. Data represent cumulative results of three independent transfers.
Figures 12A, 12B, 12C:
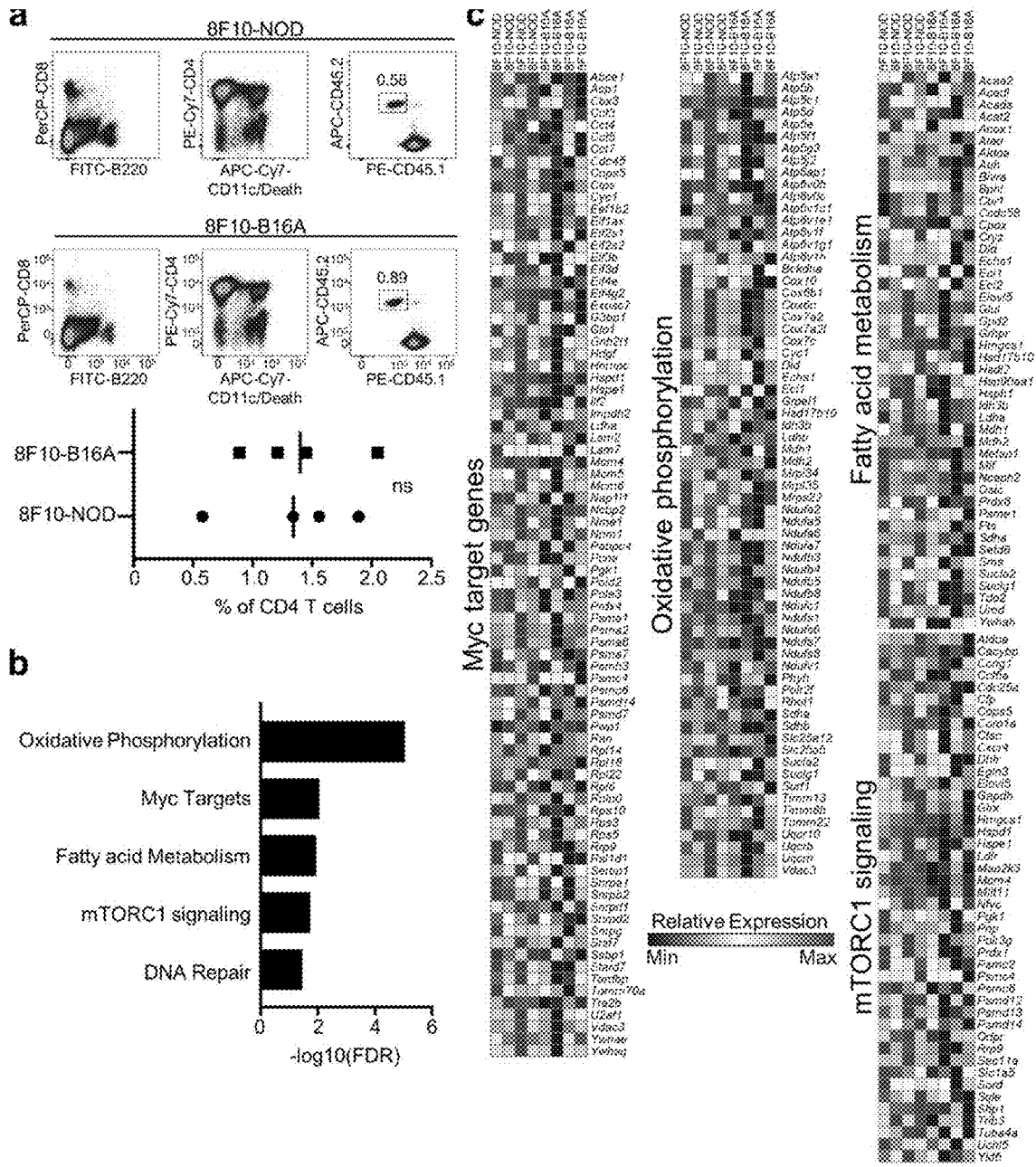
FIG. 12a-FIG. 12c: RNA-seq analysis of 8F10 T cells developed in NOD or B16A hosts. a, Representative FACS plots (top) showing the sorting strategy and recovery of 8F10 T cells from iLNs of NOD or B16A-recipient mice six weeks after adoptive transfer of bone marrow. The scatter plot (bottom) shows the percentage of recovered 8F10 T cells among total CD4 T cells from four independent experiments. ns, not significant; two-tailed paired Student's t-test. b, Biological pathways that are significantly enriched in the 8F10-NOD versus 8F10-B16A samples using GSEA and Hallmark database. c, Heat maps of all enriched genes in individual metabolic pathways depicted in FIG. 4c.

The widespread presentation of insulin peptides in lymphoid tissues influences the biology of T cells. We generated a bone marrow chimaera model in which we transferred a small number of bone marrow stem cells from CD45.2 8F10 mice deficient in T-cell receptor alpha chain (8F10$^{TCRα-/-}$) into non-lethally irradiated NOD or B16A hosts (CD45.1) (FIG. 4a). This resulted in the development of a small number of 8F10 T cells (0.5-2%) among the endogenous CD4 T-cell repertoire (FIG. 12a). We performed RNA sequencing analysis (RNA-seq) on isolated 8F10 T cells from iLNs of both hosts (FIG. 4a).

Hierarchical clustering using Pearson's correlation revealed differences between the transcriptomes of 8F10 T cells sourced from NOD (8F10-NOD) and B16A (8F10-B16A) hosts (FIG. 4b). Gene-set enrichment analysis (GSEA) showed significant correlations between transcripts that were upregulated in the 8F10-NOD T cells with biological pathways involving oxidative phosphorylation (OX-PHOS), Myc targets, fatty acid metabolism, mTOR complex 1 (mTORC1) signalling and DNA repair (FIG. 12b). The four most highly ranked gene sets (FIG. 4c) were associated with metabolic pathways, and involved transcripts encoding key kinases, intermediates and transcription factors (FIG. 12c) that have been shown to support T cell proliferation and functions[23].

Figures 13A, 13B:
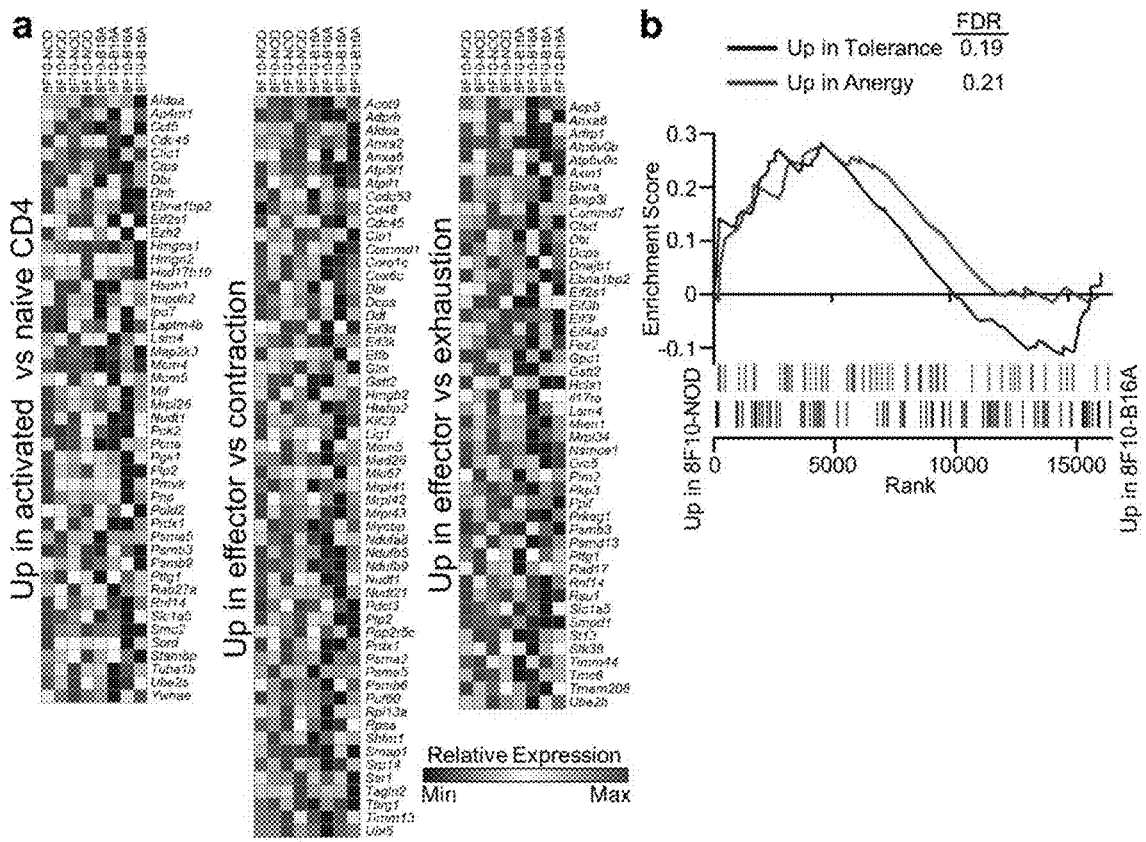
FIG. 13a-FIG. 13b: 8F10 T cells exhibit an effector phenotype, but no anergy or exhaustion phenotype, at the transcription level during peripheral antigen recognition. a, Heat maps showing all the enriched genes of the three immunological pathways illustrated in FIG. 4d. b, GSEA enrichment plots performed on differentially expressed genes in 8F10 T cells from the NOD-iLN versus B16A-iLN condition using datasets characterizing CD4 T cell anergy and CD8 T cell tolerance.

This metabolic reprogramming in 8F10 T cells from NOD mice was associated with an effector-like phenotype (FIG. 4d). The gene sets that were upregulated in these cells are also highly expressed in CD4 T cells upon stimulation[24], in CD8 T cells at the peak of expansion in comparison to the contraction phase[25], and in CD8 effectors in comparison to exhausted T cells[26]. There is little overlap among these three sets of transcripts (FIG. 13a, FIG. 4e). According to GSEA, neither T cell set correlated with anergic CD4[27] or tolerant CD8 T cells[28] (FIG. 13b).

Figures 14A, 14B, 14C, 14D, 14E, 14F:
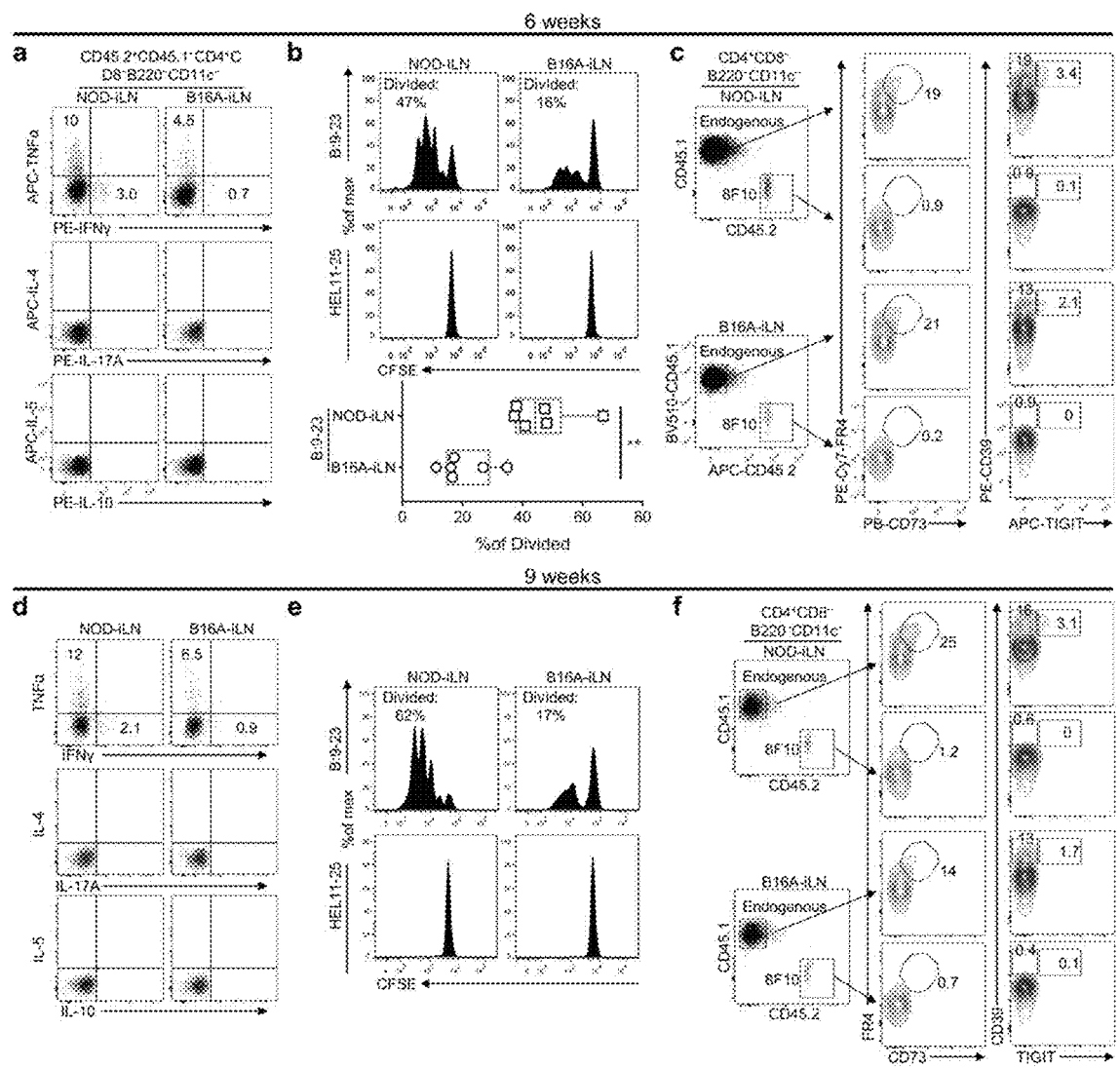
FIG. 14a-FIG. 14f: Functional analysis of 8F10 T cells developed in NOD or B16A hosts. a-f, The bone marrow chimaera was constructed as in FIG. 4a, and T cells were examined after 6 (a-c) or 9 (d-f) weeks. a, b, d, e, Bulk CD4$^+$ T cells were purified from iLNs of individual NOD or B16A mice (three per group) by two rounds of MACS negative selection. To examine cytokine repertoire (a, d), half of the individual T cell samples were combined. The remainder were kept as individual samples, labelled with CFSE (1.5 µM), and used to measure cell proliferation (b, e). In either case, T cells were mixed with NOD.Rag1$^{-/-}$ splenocytes (1:2 ratio) and stimulated with B:9-23 for 16 (a, d) or 72 (b, e) hours. a, Representative FACS plots showing intracellular cytokine staining of the 8F10 T cells from NOD-iLN or B16A-iLN, after stimulation with B:9-23 for 16 h (brefeldin A was added for the last 4 h). Production of IL-4, IL-17A, IL-5 and IL-10 was not detected. Data are representative of two independent experiments with 3 mice combined per experiment. b, Representative FACS plots (top) showing CFSE dilution of the 8F10 T cells stimulated by B:9-23 or the control HEL11-25 peptide for 72 h. The results of 6 individual mice from two independent experiments are summarized in the box plots (bottom). Box plots show the median, box edges represent the first and third quartiles, and the whiskers extend from the minimum to the maximum. **$P<0.01$, two-tailed unpaired Student's t-test. c, Representative FACS plots showing ex vivo surface staining of FR4 and CD73 as well as CD39 and TIGIT on endogenous CD4$^+$ or 8F10 T cells in the iLNs of NOD or B16A mice. Data are representative of three mice analyzed in two independent experiments. d-f, Experiments were performed in week 9 following the procedures described in a-c. The data in d-f are from a single experiment.

Functional analysis at the six-week time point revealed a higher capacity of effector cytokine (TNF and IFNγ) production (FIG. 14a) and cell proliferation (FIG. 14b) in 8F10-NOD T cells. Neither T cell set expressed molecules associated with anergy and exhaustion[26,27,29] (FIG. 14c). Similar results were obtained for T cells analyzed nine weeks after the bone marrow transfer (FIG. 14d-f). Of note, when the two sets of T cells were transferred into NOD.Rag1$^{-/-}$ recipients, the onset of diabetes was accelerated by the 8F10-NOD set (FIG. 4f). Therefore, 8F10 T cells acquired an effector-like phenotype during peripheral antigen recognition, supported by transcriptional reprogramming and increased diabetogenicity.

In summary, peptide exocytosis is a normal response of β-cells that represents a mechanism of communication with the lymphoid tissues. Similar mechanisms may apply to other endocrine organs that also contain crinophagic granules. Examining the released peptides may enable better-targeted identification of T cell responses; a set of responses that could be extensive, given the diversity of exocytosed moieties. Previous studies have shown that ablation of all lymph nodes eradicates the pathogenic T cell repertoire and abolishes diabetes[30], emphasizing the importance of the entire lymphatic system in interactions with T cells. Finally, the biological outcomes described here for 8F10 T cells may vary for other insulin-reactive T cells with divergent TCR affinities. Comprehensive understanding of these outcomes will require analysis of the entire insulin-reactive T cell pool at different stages of the disease.

Methods

Mice

NOD/ShiLtJ (NOD), NOD.129S7(B6)-Rag1$^{tm1Mom}$/J (NOD.Rag1$^{-/-}$), NOD.Cg-Tg(Ins2*Y16A) 1EllIns1$^{tm1mJja}$Ins2$^{tm1Jja}$/GseJ (NOD.B16A), NOD.Cg-Tg (TcraTcrbNY8.3)1Pesa/DvsJ (8.3), NOD.129S2(B6)-Ighm$^{tm1Cgn/DoiJ}$ (μMT), NOD.C-(Ptprc-D)1Mit262)/WehiJ (NOD.CD45.2), NOD.B10Sn-H2b/J (NOD.H2b) and B6.NOD-(D17Mit21-D17Mit10)/LtJ (B6g7) mice were originally obtained from the Jackson Laboratory. NOD.10E11 TCR transgenic mice (TCRα: TRAV5D-4/TRAJ42; TCRβ: TRBV13-3/TRBD2/TRBJ2-7) were generated using a previous protocol[5]. NOD.4F7 TCR transgenic mice, NOD.Aire$^{-/-}$, and NOD.TCRα$^{-/-}$ mice were generated by M.S.A. The 8F10 or 10E11 mice expressing the CD45.2 allotype were generated by intercrossing the original TCR transgenic line (CD45.1) with the NOD.CD45.2 mice, and the CD45.2.NOD.8F10 mice were further crossed with the NOD.TCRα$^{-/-}$ mice to generate the CD45.2 8F10$^{TCRα-/-}$ mice. B6.Rag1$^{-/-}$ mice were used to intercross with B6g7 mice to generate B6g7.Rag1$^{-/-}$ mice. All mice were bred and maintained under specific pathogen-free conditions in our animal facility. All experiments were approved by the Division of Comparative Medicine of Washington University School of Medicine in St. Louis (Accreditation number A3381-01).

Human Pancreatic Islets

De-identified human primary islets isolated from deceased donors were obtained from Prodo Laboratories. Experiments were judged to be 'not human subject research' by Washington University Human Research Protection Office (IRB ID #201801183; Federalwide Assurance #FWA00002284). In total, islets from three donors were used: donor 1 (female, 57 years, BMI 21.35), donor 2 (female, 49 years, BMI 33), donor 3 (male, 28 years, BMI 34.7). Purity of the islets was between 85 and 98%. Islets were cultured in CMRL medium supplemented with 10% FBS and 50% L-cell conditioned medium[31] for recovery. The granules were isolated from ~1500 islets after 1-3 days of culture.

Antibodies

The following fluorescently conjugated antibodies were purchased from BioLegend: anti-B220 (RA3-6B2), anti-CD11c (N418), anti-CD4 (RM4-5), anti-CD45 (30-F11), anti-CD45.1 (A20), anti-CD45.2 (104), anti-CD8a (53-6.7), anti-F4/80 (BM8), anti-Vβ8.1/8.2 (KJ16-133.18), anti-CD44 (IM7), anti-CD62L (MEL-14), anti-CD25 (PC61.5) and anti-TNFα (MP6-XT22). Unconjugated or Alexa Fluor 647-labelled Rabbit anti-insulin monoclonal antibody (C27C9) was purchased from Cell Signaling Technology. Unconjugated mouse anti-insulin monoclonal antibody (E11D7) was purchased from Millipore. Alexa Fluor 594 F(ab)$_2$ donkey anti-mouse IgG and HRP-conjugated goat anti-mouse IgG (Fcγ-specific) were purchased from Jackson ImmunoResearch.

Flow Cytometry and Cell Sorting

Flow cytometry analysis was done as previously described[7]. The samples were examined using a FACSCanto II (BD Biosciences) and the data were analyzed using FlowJo software (Tree Star Software). CD4$^+$ T cells from iLNs were enriched using the CD4$^+$ T cell isolation kit (Miltenyi Biotech), the 8F10 T cells were sorted as CD45.2$^+$CD45.1$^-$CD4$^+$CD8$^-$B220$^-$CD11c$^-$ using FACSAria II (BD Biosciences).

CFSE and CMTMR Labelling

For two-photon imaging, naive CD4 T cells were purified by two rounds of MACS negative selection using the naive CD4$^+$ T cell isolation kit (Miltenyi Biotech) to remove non-CD4 and CD44$^+$ T cells. The CD25$^+$ cells were further removed from the flow-through portion using the CD25 microbead kit (Miltenyi Biotech). The naive 8.3 or wild-type CD8 T cells were purified similarly by using the naive CD8$^+$ T cell isolation kit. Flow cytometry analysis confirmed that >95% of the cells were CD4$^+$/CD8$^+$CD25$^-$CD62L$^{hi}$CD44$^-$. CFSE (carboxyfluorescein succinimidyl ester) or 5-(and-6)-(((4-chloromethyl)benzoyl)amino)tetramethylrhodamine (CMTMR) labelling was performed using the Vybrant CFDA s.e. Cell Tracer Kit and the CellTracker Orange CMTMR Dye (both from ThermoFisher Scientific), respectively. In brief, T cells (10$^7$/ml in PBS) were incubated with 10 μM CFSE or 8 μM CMTMR for 25 min at 37° C. with a gentle shake after 10 min. Under these conditions, T cells were labelled with satisfactory intensities without significant cell death. Ice-cold PBS was then added to quench the labelling.

Adoptive Transfer

CFSE- or CMTMR-labelled T cells were mixed 1:1 and were injected intravenously. For all the two-photon experiments, 2×10$^6$ T cells with either label were transferred. Varying T cell numbers in preliminary experiments determined that this amount resulted in a stable 0.5-0.8% reconstitution of the transferred T cells in the endogenous CD4 T cell pool, which was sufficient for two-photon imaging without causing obvious intraclonal competition. All the recipient mice were 3-4-week-old female mice unless otherwise mentioned. For experiments in FIG. 4f, FACS-sorted 8F10 T cells from pooled iLNs of 8-10 NOD or B16A mice were adoptively transferred intravenously into 4-6-week old NOD. Rag1÷ recipients (10$^5$ cells per mouse).

Two-Photon Imaging

Lymph nodes were removed, attached to coverslips, placed in $CO_2$-independent medium (Gibco) at room temperature and immediately imaged in a perfusion chamber to simulate blood flow (36.5° C. DMEM; 95% $O_2$ and 5% $CO_2$). Two-photon microscopy images were collected using a customized Leica SP8 Two-Photon Microscope (Leica Microsystems) equipped with a 25× and 0.95 numerical aperture water-immersion objective and a Mai Tai HP Deep-See Laser (Spectra-Physics) tuned to 840 nm. Fluorescence emission was guided directly to external hybrid photodetectors (Leica/Hamamatsu). For signal separation, we used three separate dichroic beam splitters without bandpass filters (Semrock): 484-nm edge BrightLine (FF484-FDi01), 495-nm edge BrightLine (FF495-Di03), and 560-nm edge BrightLine (FF560-Di01). The mirrors were arranged in dendritic fashion. Stacks were collected with 2.5 μm between images with 25-30 images per stack.

For cell tracking, two or three regions of one lymph node were randomly selected and cropped. Cells were tracked manually in 3D volume using Imaris 8.41 software (Bitplane). We tracked the first 11 time points from each track (representing 5 min and 10 velocities between the time points). Each dot represents the mean velocity out of the 10 that were tracked. We also calculated the meandering index and the motility coefficient for each track. Note that we chose tracks with the same length since the track length impacts these last two parameters. The meandering index and the motility coefficient data are not shown for space reasons however the results support the velocity data. The mean track velocities (μm/min) were calculated for individual tracks as previously described[11].

Surgical Removal of Pancreatic Lymph Nodes

NOD mice (3-week old) were anesthetized with a 4% mixture of isoflurane in oxygen. The two pLNs were exposed by gently retracting the spleen, pancreas, stomach and intestines, and were grasped with blunt forceps. Using an ophthalmic cautery on low power, the blood vessels on either side of the pLNs were cauterized and the pLNs were removed. The sham surgery was performed with the same procedures except that the pLNs were exposed without removal.

S961 Administration

The S961 peptide (GSLDESFYDWFER-QLGGGSGGSSLEEEWAQIQCEVWGRGCPSY (SEQ ID NO: 33)) was synthesized by LifeTein, with an intrachain disulphide bridge between Cys33 and Cys40 (underlined). S961 (20 nMol/week) or control PBS was filled into the Alzet osmotic pump (2001 model, Durect) and inserted subcutaneously in the back of anaesthetized mice through an incision between scapula. Blood glucose levels were monitored twice a day (Chemstrip 2GP; Roche); mice with a level above 250 mg/dl for two consecutive measurements were considered diabetic.

Competitive ELISA Assay 96-well ELISA plates were coated with human insulin solution (1 μg/well) or peptides B:1-30 or B:9-23 (2 μM), and were blocked with 3% BSA overnight at 4° C. Soluble competitive inhibitors, including different synthetic peptides and biological samples, were pre-incubated with the E11D7 (100 ng/ml), 6F3.B8 (20 ng/ml), or AIP (4 ng/ml) monoclonal antibodies for 30 min and the mixture was added to the plate-bound antigens for 1 h at room temperature. In the absence of soluble competitive inhibitors, these concentrations of the monoclonal antibodies resulted in about a 50% binding to the plate-bound antigens. HRP-conjugated goat anti-mouse IgG (1:10000) antibody was then added for 1 h; the responses were developed using the OptEIA TMB Substrate (BD). The data ($A_{450\ nm}$) were collected using an iMark Microplate Reader (Bio-Rad Laboratories). For quantifying the biological samples, each experiment was paired with a standard curve in which serially diluted amounts of soluble antigens were used to suppress the binding of their cognate monoclonal antibodies to the same antigen in the plate-bound form. The degree of inhibition by the biological samples was calculated relative to the blocking curve used by the specific antigen using an equation generated by linear regression of the standard curve.

Immunofluorescence Microscopy

Mouse islets were isolated as previously described[7]. The islets were blocked with normal goat serum, fixed with 4% methanol-free formaldehyde, permeabilized with 0.2% saponin (Sigma), and stained with AIP or 6F3.B8 (50 μg/ml) for 45 min on ice. The samples were then stained with Alexa Fluor 594 F(ab)$_2$ donkey anti-mouse IgG (30 μg/ml), Alexa Fluor 647 Rabbit anti-insulin (20 μg/ml), and Alexa Fluor 488 anti-mouse CD11c (40 μg/ml) for 45 min on ice and mounted using the Prolong Diamond mountant (ThermoFisher). The samples were viewed using the Eclipse E800 microscope (Nikon) equipped with the EXi Blue fluorescence camera (Qimaging).

Electron Microscopy with Immunogold

Islets were fixed in 4% paraformaldehyde (Polysciences) in 100 mM PIPES, 0.5 mM $MgCl_2$, pH 7.2 for 1 h at 4° C. Samples were embedded in 10% gelatin and infiltrated overnight with 2.3 M sucrose/20% polyvinyl pyrrolidone in PIPES/$MgCl_2$ at 4° C. Ultrathin sections of 50 nm were incubated with a blocking solution supplemented with 5% FBS and 5% normal goat serum for 30 min and subsequently incubated with rabbit anti-insulin (C27C9) and mouse anti-B chain (6F3.B8) antibodies for 1 h at room temperature. Sections were subsequently incubated with goat anti-mouse IgG conjugated to 18 nm colloidal gold and goat anti-rabbit IgG antibody conjugated to 12 nm colloidal gold for 1 h. Sections were stained with uranyl acetate and lead citrate and viewed on a JEOL 1200 EX transmission electron microscope (JEOL USA) equipped with an AMT 8-megapixel digital camera and AMT Image Capture Engine v.602 software (Advanced Microscopy Techniques). All labelling experiments were conducted in parallel with controls omitting the primary antibody. These controls were consistently negative.

Insulin Secretion Assay

Islets were equilibrated in DMEM supplemented with 10% FBS and 5.5 mM glucose for 24 h in 24-well plates. The medium was then replaced with 300 μl pre-warmed Krebs-Ringer-HEPES balance solution containing 0.2% BSA with 2.5 mM or 25 mM glucose. After 1 h incubation, the culture supernatants were collected for the competitive ELISA assay or mass spectrometry analysis.

β-Cell Granule Isolation

Mouse and human islets were dispersed using non-enzymatic dispersion solution (Sigma). Cells were resuspended in PBS and lysed by passing them through a cell homogenizer (Isobiotec). The lysate was centrifuged twice for 10 min at 500 g, 4° C. to pellet cell debris. The supernatant was centrifuged for 10 min at 5,000 g, 4° C. The 5,000 g spin was repeated on the supernatant and the two pellets were combined. This fraction was highly enriched in peptide-containing vesicles compatible with the crinophagic bodies, and as such have been labelled. This fraction may also contain organelles other than the insulin-containing ones. The supernatant after the 5,000 g spin was centrifuged for 30 min at 25,000 g, 4° C. to pellet secretory granules. This supernatant was discarded, and the 25000 g pellet was suspended in 100 µl PBS. The microcentrifuge used for granule isolation was an Eppendorf 5417R (Eppendorf) with a FA45-24-11 fixed angle rotor. Fractions were frozen at −80° C. and thawed at 37° C. for five cycles to release the contents of granules. After freeze-thaw, complete protease inhibitor cocktail was added to the sample which was then concentrated by Speed-Vac to <100 µl. The sample was passed through C18 Ziptips (Pierce) and peptides then were eluted in 0.1% formic acid/95% acetonitrile and then dried with a SpeedVac.

Sample Preparation for Mass Spectrometry Analysis

Biological samples were treated with 2.5% trifluoroacetic acid (TFA) to a final concentration of 0.36% (v/v), and the peptides were purified using the C18 Ziptips, eluted with 0.1% formic acid in 95% acetonitrile, and lyophilized. For peptide capture, TFA-adjusted mouse urine (12 ml) was cleaned up using C18 Sep Pak cartridges (Waters). The analytes retained by the cartridge sorbent were eluted with methanol, lyophilized, and reconstituted with 2 ml sterile PBS. The material was then incubated with a 1:1 mixture of sepharose pre-conjugated with AIP or 6F3.B8 monoclonal antibodies (1 ml slurry total) for 72 h at 4° C. with gentle rotation. The urine-sepharose mixture was poured into a Bio-Rad Econo column, and after extensive washing, the antibody-bound material was eluted with 10% acetic acid and lyophilized.

Mass Spectrometry

A Dionex UltiMate 1000 system (Thermo Scientific) was coupled to an Orbitrap Fusion Lumos (Thermo Scientific) through an EASY-Spray ion source (Thermo Scientific). Peptide samples were loaded (30 µl/min, 1 min) onto a trap column (100 µm×2 cm, 5 µm Acclaim PepMap 100 C18, 50° C.), eluted (300 µl/min) onto an EASY-Spray PepMap RSLC C18 column (2 µm, 25 cm×75 µm ID, 50° C., Thermo Scientific) and separated with the following gradient, all % Buffer B (0.1% formic acid in ACN): 0-40 min, 2-22%; 40-50 min, 22-35%; 50-60 min, 35-95%; 60-70 min, isocratic at 95%; 70-71 min, 95-2%, 71-85 min, isocratic at 2%. Spray voltage was 1900 V, ion transfer tube temperature was 275° C., and RF lens was 30%. Mass spectrometry scans were acquired in profile mode and MS/MS scans in centroid mode, for ions with charge states 2-7, with a cycle time of 3 s. For HCD, mass spectra were recorded from 375-1500 Da at 120K resolution (at m/z=200), and MS/MS were triggered above a threshold of $2.5 \times 10^4$, with quadrupole isolation (1.6 Da) at 30K resolution, and collision energy of 30%. Dynamic exclusion was used (35 s). For high SA EThcD, mass spectra were acquired from 350-1500 Da at 60K resolution, and MS/MS spectra were triggered for ions above a threshold of $5 \times 10^4$ with quadrupole isolation (0.7 Da) at 15K resolution. Fragmentation employed calibrated charge-dependent ETD, with SA (40%) applied in the HCD cell. Dynamic exclusion was used (60 s). For low SA EThcD, mass spectra were recorded from 375-1500 Da at 120K resolution (at m/z=200), and MS/MS spectra were acquired for ions above a minimum intensity threshold of $2.5 \times 10^4$ at 15K resolution. ETD reaction time was fixed at 100 ms, with SA (15%) applied in the HCD collision cell.

Mass Spectrometry Data Analysis

Data files were uploaded to PEAKS 8.0 (Bioinformatics Solutions) for processing, de novo sequencing and database searching. Resulting sequences were searched against the UniProt Mouse Proteome database (downloaded 8 Jun. 2017; 25,144 entries) with mass error tolerances of 20 ppm and 0.02 Da for parent and fragment, respectively, no enzyme specificity and no fixed or variable modifications. The Common Repository for Adventitious Proteins database (www.thegpm.org/crap/) was used to identify contaminant proteins. FDR estimation was enabled. Peptides were filtered for −10 log P 20, and proteins were filtered for −10 log P 30 and one unique peptide. For all experiments, this gave an FDR of <1% at the peptide-spectrum match level. Peptides matching to insulin-1 and insulin-2 were manually verified by visual inspection. For relative quantification, peak areas for all manually verified peptides were exported from PEAKS, normalized to the total ion current, and $\log_2$ transformed.

T Cell Stimulation and Antigen Presentation Assay

In FIG. 5$i$, ConA-stimulated peritoneal macrophages were treated with 0.2 or 1 µM S961 for 1 h at 37° C. and were then cultured with the IIT-3 T cell hybridoma that recognizes the 13-21 peptide, in the presence of serially diluted insulin (19278; Sigma). In FIG. 6$e$, C3g7 cells were treated with chloroquine for 2 h at 37° C., washed, pulsed with the antigens, and cultured with T cell hybridomas. After incubation for 18 h, the culture supernatants were assayed for IL-2 production.

Bone Marrow Chimaera

The female donor 8F10.TCRα$^{-/-}$ (CD45.2) mice were injected intraperitoneally with fluorouracil (200 mg/kg), and bone marrow cells were isolated from the femur and tibia on day 5. The cells were adoptively transferred into sublethally irradiated (600 rads) 3-week old female NOD or B16A hosts ($10^4$/mouse).

RNA-Seq Analysis

Total RNA was isolated using the Ambion RNAqueous-Micro kit (Thermo Fisher Scientific). RNA-seq library preparation and sequencing was performed as previously described[32]. The differential expression analysis was done with the DESeq2 package (version 1.18.1). Multifactor analysis was used to account for donor effect. Specifically, paired 8F10-NOD and 8F10-B16A samples from one isolation (four pairs in total) were treated as one donor group. Gene set enrichment pathways analysis was done using the Broad Institute's GSEA software and MSigDB Hallmark or C7 immunological signatures databases. The latter included datasets: GSE28726[24], GSE1000001_1577_200_UP[25], GSE9650[26] and GSE32025[28]. All heat maps are in $\log_2$ scale. The gene expression matrix counts were adjusted for donor effect with Combat (sva package) only for heat maps and clustering.

Statistics

Mice were age and gender matched. Among the mice with matched ages and genders, they were randomized and distributed equally into experimental groups. Power analysis was used to estimate the sample size in some experiments, as described in the Reporting Summary. The investigators were not blinded to allocation during experiments and outcome assessment. One-way ANOVA with Sidak's multiple comparisons test was used to determine significant differences among multiple groups with unpaired biological replicates. The two-tailed unpaired Student's t-test was used to determine significant differences between two groups with unpaired biological replicates. The two-tailed paired Student's t-test was used to calculate P values of each pair of independent experiments. The log-rank test was used to determine the significant difference of diabetes incidence.

Data Availability

The RNA-seq data have been deposited in the Gene Expression Omnibus under accession number GSE114824. The mass spectrometry proteomics data have been deposited to the ProteomeXchange Consortium via the PRIDE partner repository with the dataset identifier PXD009919.

Insulin peptides (static-content.springer.com/esm/art % 3A10.1038%2Fs41586-018-0341-6/MediaObjects/41586_2018_341_MOESM2_ESM.xlsx) identified in mouse and human granules.

Islet secretion insulin peptide list (static-content.springer.com/esm/art % 3A10.1038%2Fs41586-018-0341-6/MediaObjects/41586_2018_341_MOESM3_ESM.xlsx).

Motility of anti-HEL 10E11 T cells in mice given HEL. The anti-HEL 10E11 (green) and WT polyclonal (red) CD4 T cells were adoptively transferred into NOD mice given indicated amounts of HEL protein. On day 3 post transfer, the inguinal lymph nodes were harvested and imaged by two-photon microscopy. Videos (shown here: static-content.springer.com/esm/art % 3A10.1038%2Fs41586-018-0341-6/MediaObjects/41586_2018_341_MOESM4_ESM.mov) show a progressive reduction of the 10E11 T cell velocities as the antigen amount increases.

Motility of anti-insulin peptide 8F10 T cells in lymph nodes. The insulin peptide-reactive 8F10 (green) and WT (red) CD4 T cells were adoptively transferred into NOD mice. On day 3 post transfer, the pancreatic (pLN), inguinal (iLN), and axillary (aLN) lymph nodes were imaged. The videos (shown here: static-content.springer.com/esm/art % 3A10.1038%2Fs41586-018-0341-6/MediaObjects/41586_2018_341_MOESM5_ESM.mov) depict a reduction of the 8F10 T cell motility relative to the WT controls in all the lymph nodes.

Motility of anti-insulin peptide 8F10 T cells in the absence of the antigen. The insulin peptide-reactive 8F10 (green) and WT (red) CD4 T cells were adoptively transferred into B16A mice that lack immunogenic insulin peptides. On day 3 post transfer, the pancreatic (pLN) and inguinal (iLN) lymph nodes were imaged. The videos (shown here: static-content.springer.com/esm/art % 3A10.1038%2Fs41586-018-0341-6/MediaObjects/41586_2018_341_MOESM6_ESM.mov) depict a comparable level of velocities between the 8F10 and WT T cells in the B16A hosts.

Motility of anti-insulin 4F7 T cells in mice with in vivo blockade of insulin receptor. The insulin-reactive 4F7 (green) and WT (red) CD4 T cells were adoptively transferred into NOD mice that were infused with PBS or the insulin receptor antagonist S961. On day 3 post transfer, the inguinal (iLN) lymph nodes were imaged. The videos (shown here: static-content.springer.com/esm/art % 3A10.1038%2Fs41586-018-0341-6/MediaObjects/41586_2018_341_MOESM7_ESM.mov) depict a partial reduction of the 4F7 T cell motility influenced by S961 treatment relative to the PBS control.

Motility of anti-insulin peptide 8F10 T cells in mice with in vivo blockade of insulin receptor. The insulin peptide-reactive 8F10 (green) and WT (red) CD4 T cells were adoptively transferred into NOD mice that were infused with PBS or the insulin receptor antagonist S961. On day 3 post transfer, the inguinal (iLN) lymph nodes were imaged. The videos (shown here: static-content.springer.com/esm/art % 3A10.1038%2Fs41586-018-0341-6/MediaObjects/41586_2018_341_MOESM8_ESM.mov) depict a comparable level of motility arrest in the 8F10 T cells relative to WT T cells between mice infused with PBS and S961.

REFERENCES

1. Nakayama, M. et al. Prime role for an insulin epitope in the development of type 1 diabetes in NOD mice. *Nature* 435, 220-223 (2005).
2. Unanue, E. R. Antigen presentation in the autoimmune diabetes of the NOD mouse. *Annu. Rev. Immunol.* 32, 579-608 (2014).
3. Mohan, J. F. et al. Unique autoreactive T cells recognize insulin peptides generated within the islets of Langerhans in autoimmune diabetes. *Nat. Immunol.* 11, 350-354 (2010).
4. Mohan, J. F., Petzold, S. J. & Unanue, E. R. Register shifting of an insulin peptide-MHC complex allows diabetogenic T cells to escape thymic deletion. *J. Exp. Med.* 208, 2375-2383 (2011).
5. Mohan, J. F., Calderon, B., Anderson, M. S. & Unanue, E. R. Pathogenic CD4$^+$ T cells recognizing an unstable peptide of insulin are directly recruited into islets bypassing local lymph nodes. *J. Exp. Med.* 210, 2403-2414 (2013).
6. Vomund, A. N. et al. Beta cells transfer vesicles containing insulin to phagocytes for presentation to T cells. *Proc. Natl Acad. Sci. USA* 112, E5496-E5502 (2015).
7. Wan, X., Thomas, J. W. & Unanue, E. R. Class-switched anti-insulin antibodies originate from unconventional antigen presentation in multiple lymphoid sites. *J. Exp. Med.* 213, 967-978 (2016).
8. Wan, X. & Unanue, E. R. Unique features in the presentation of insulin epitopes in autoimmune diabetes: an update. *Curr. Opin. Immunol.* 46, 30-37 (2017).
9. Egen, J. G. et al. Intravital imaging reveals limited antigen presentation and T cell effector function in mycobacterial granulomas. *Immunity* 34, 807-819 (2011).
10. Le Borgne, M. et al. The impact of negative selection on thymocyte migration in the medulla. *Nat. Immunol.* 10, 823-830 (2009).
11. Zinselmeyer, B. H. et al. In situ characterization of CD4$^+$ T cell behavior in mucosal and systemic lymphoid tissues during the induction of oral priming and tolerance. *J. Exp. Med.* 201, 1815-1823 (2005).
12. Eickhoff, S. et al. Robust anti-viral immunity requires multiple distinct T cell-dendritic cell interactions. *Cell* 162, 1322-1337 (2015).
13. Verdaguer, J. et al. Spontaneous autoimmune diabetes in monoclonal T cell nonobese diabetic mice. *J. Exp. Med.* 186, 1663-1676 (1997).
14. Schäffer, L. et al. A novel high-affinity peptide antagonist to the insulin receptor. Biochem. *Biophys. Res. Commun.* 376, 380-383 (2008).
15. Gardner, J. M. et al. Deletional tolerance mediated by extrathymic Aire-expressing cells. *Science* 321, 843-847 (2008).
16. Smith, R. E. & Farquhar, M. G. Lysosome function in the regulation of the secretory process in cells of the anterior pituitary gland. *J. Cell Biol.* 31, 319-347 (1966).
17. Halban, P. A. & Wollheim, C. B. Intracellular degradation of insulin stores by rat pancreatic islets in vitro. An alternative pathway for homeostasis of pancreatic insulin content. *J. Biol. Chem.* 255, 6003-6006 (1980).
18. Weckman, A. et al. Autophagy in the endocrine glands. *J. Mol. Endocrinol.* 52, R151-R163 (2014).
19. Yang, J. et al. Autoreactive T cells specific for insulin B:11-23 recognize a low-affinity peptide register in human subjects with autoimmune diabetes. *Proc. Nati Acad. Sci. USA* 111, 14840-14845 (2014).
20. Wong, F. S. et al. Identification of an MHC class I-restricted autoantigen in type 1 diabetes by screening an organ-specific cDNA library. *Nat. Med.* 5, 1026-1031 (1999).

21. Lamont, D. et al. Compensatory mechanisms allow undersized anchor-deficient class I MHC ligands to mediate pathogenic autoreactive T cell responses. *J. Immunol.* 193, 2135-2146 (2014).
22. Chen, W. et al. Evidence that a peptide spanning the B-C junction of proinsulin is an early Autoantigen epitope in the pathogenesis of type 1 diabetes. *J. Immunol.* 167, 4926-4935 (2001).
23. Buck, M. D., O'Sullivan, D. & Pearce, E. L. T cell metabolism drives immunity. *J. Exp. Med.* 212, 1345-1360 (2015).
24. Constantinides, M. G., Picard, D., Savage, A. K. & Bendelac, A. A naive-like population of human CD1d-restricted T cells expressing intermediate levels of promyelocytic leukemia zinc finger. *J. Immunol.* 187, 309-315 (2011).
25. Kaech, S. M., Hemby, S., Kersh, E. & Ahmed, R. Molecular and functional profiling of memory CD8 T cell differentiation. *Cell* 111, 837-851 (2002).
26. Wherry, E. J. et al. Molecular signature of CD8+ T cell exhaustion during chronic viral infection. *Immunity* 27, 670-684 (2007).
27. Macian, F. et al. Transcriptional mechanisms underlying lymphocyte tolerance. *Cell* 109, 719-731 (2002).
28. Schietinger, A., Delrow, J. J., Basom, R. S., Blattman, J. N. & Greenberg, P. D. Rescued tolerant CD8 T cells are preprogrammed to reestablish the tolerant state. *Science* 335, 723-727 (2012).
29. Kalekar, L. A. et al. CD4+ T cell anergy prevents autoimmunity and generates regulatory T cell precursors. *Nat. Immunol.* 17, 304-314 (2016).
30. Levisetti, M. G., Suri, A., Frederick, K. & Unanue, E. R. Absence of lymph nodes in NOD mice treated with lymphotoxin-β receptor immunoglobulin protects from diabetes. *Diabetes* 53, 3115-3119 (2004).
31. Aly, H. et al. A novel strategy to increase the proliferative potential of adult human β-cells while maintaining their differentiated phenotype. *PLoS One* 8, e66131 (2013).
32. Ferris, S. T. et al. The islet-resident macrophage is in an inflammatory state and senses microbial products in blood. *J. Exp. Med.* 214, 2369-2385 (2017).

---

What is claimed is:

1. A method of detecting insulin peptides comprising:
administering glucose to a subject;
obtaining a biological sample comprising circulating blood cells from the subject; and
detecting a level of an immunogenic insulin peptide from the circulating blood cells, wherein the immunogenic insulin peptide comprises a pathogenic epitope and is derived from an insulin B-chain.

2. The method of claim 1, wherein the circulating blood cells are circulating leukocytes.

3. The method of claim 1, wherein the immunogenic insulin peptide is a peptide fragment catabolized from insulin released from pancreatic islets into blood.

4. The method of claim 1, wherein the immunogenic insulin peptide is recognized by insulin-specific CD4 T cells.

5. The method of claim 4, wherein the insulin-specific CD4 T cells are segment 12-20 insulin B-chain (B: 12-20)-specific CD4 T cells recognizing a B: 12-20 epitope.

6. The method of claim 5, wherein the B:12-20-specific T cells have reduced motility when in fluid contact with immunogenic insulin peptides compared to a control in fluid contact with the immunogenic insulin peptides.

7. The method of claim 6, wherein the control is a wild-type CD4 T cell.

8. The method of claim 1, wherein the level of the immunogenic insulin peptide is detected using mass spectrometry.

9. The method of claim 8, wherein peptide components in the biological sample are separated with a gradient: all % Buffer B (0.1% formic acid in acetonitrile (ACN)): at about 0-40 min, at about 2-22%; at about 40-50 min, at about 22-35%; at about 50-60 min, at about 35-95%; at about 60-70 min, isocratic at about 95%; at about 70-71 min, at about 95-2%; and at about 71-85 min, at about isocratic at 2%.

10. The method of claim 1, wherein the method further comprises:
comparing the detected level of the immunogenic insulin peptide to a level of immunogenic insulin peptides of a control subject not having Type 1 Diabetes (T1D);
comparing the detected level of the immunogenic insulin peptide to a level of immunogenic insulin peptide of the subject prior to a T1D treatment; or
comparing the detected level of the immunogenic insulin peptides to a level of immunogenic insulin peptide of the subject at an earlier time.

11. The method of claim 10, wherein if the detected level of the immunogenic insulin peptide is elevated compared to the control subject not having T1D, the subject is diagnosed with T1D or is determined to be at risk for developing T1D.

12. The method of claim 10, wherein if the detected level of the immunogenic insulin peptide is elevated compared to the level of immunogenic insulin peptide of the subject prior to the T1D treatment, the subject is determined to be not responding to the T1D treatment.

13. The method of claim 10, wherein if the detected level of the immunogenic insulin peptide is equivalent or reduced compared to the level of immunogenic insulin peptide of the subject prior to the T1D treatment, the subject is determined to be responding to the T1D treatment.

14. The method of claim 10, wherein if the detected level of the immunogenic insulin peptide is elevated compared to the level of immunogenic insulin peptide of the subject at an earlier time, the subject is determined to have an increased stage of disease.

15. The method of claim 1, wherein the immunogenic insulin peptide comprises an immunogenic insulin peptide epitope, immunogenic portion of an immunogenic insulin peptide, or immunogenic mutant of an insulin peptide and is capable of eliciting an autoimmune response in the subject.

16. The method of claim 1, wherein the immunogenic insulin peptide is a peptide comprising or derived from B: 9-23 peptides.

17. The method of claim 1, wherein the immunogenic insulin peptide is derived from an insulin B: 9-23 segment or derived from a portion of an insulin B: 9-23 segment, is immunogenic, and comprises or is derived from at least a portion of the insulin B chain, an immunogenic mutant thereof, or an immunogenic fragment thereof.

18. The method of claim 1, wherein the immunogenic insulin peptide is selected from the group consisting of:

FVNQHLCGSH; (SEQ ID NO: 1)

FVNQHLCGSHLVE; (SEQ ID NO: 2)

```
                                    (SEQ ID NO: 3)
FVNQHLCGSHLVEALYLVCGERGFFYTPKT;

(SEQ ID NO: 4)
FVNQHLcGSHLVEALYLVcGERGFFYTPKT;

(SEQ ID NO: 5)
HLVEALY;

(SEQ ID NO: 6)
LVEALYLVCGERGFFYTPKT;

(SEQ ID NO: 7)
GERGFFYTPK;

(SEQ ID NO: 8)
GERGFFYTPKT;

(SEQ ID NO: 9)
ERGFFYTPKT;

(SEQ ID NO: 10)
GFFYTPKT;

(SEQ ID NO: 11)
FFYTPK;

(SEQ ID NO: 12)
FFYTPKT;

(SEQ ID NO: 13)
REAEDLQVGQVELGGGPGAGSLQPLALEGSLQ;

(SEQ ID NO: 14)
EAEDLQVG;

(SEQ ID NO: 15)
EAEDLQVGQ;

(SEQ ID NO: 16)
EAEDLQVGQVE;

(SEQ ID NO: 17)
EAEDLQVGQVEL;

(SEQ ID NO: 18)
EAEDLQVGQVELG;

(SEQ ID NO: 19)
EAEDLQVGQVELGG;

(SEQ ID NO: 20)
FVNQHLcGSHLVEALYLVcGERGFFYTPKT;

(SEQ ID NO: 21)
HLVEALY;

(SEQ ID NO: 22)
GERGFFYTPKT;

(SEQ ID NO: 23)
ERGFFYTPKT;

(SEQ ID NO: 24)
GFFYTPKT;

(SEQ ID NO: 25)
FFYTPKT;

(SEQ ID NO: 26)
REAEDLQVGQVELGGGPGAGSLQPLALEGSLQ;

(SEQ ID NO: 27)
EAEDLQVGQ;

(SEQ ID NO: 28)
EAEDLQVGQVE;

(SEQ ID NO: 29)
EAEDLQVGQVEL;

(SEQ ID NO: 30)
YQLENYCN;
``` and combinations thereof.

* * * * *